(12) United States Patent
Ran et al.

(10) Patent No.: US 11,883,160 B2
(45) Date of Patent: Jan. 30, 2024

(54) POSITIONING METHOD OF FUNCTIONAL ROTATION CENTER OF SHOULDER BASED ON RIGID UPPER ARM MODEL

(71) Applicant: CHINA NATIONAL INSTITUTE OF STANDARDIZATION, Beijing (CN)

(72) Inventors: Linghua Ran, Beijing (CN); Zijian Zhou, Beijing (CN); Hongqi Xu, Beijing (CN); Xin Zhang, Beijing (CN); Chaoyi Zhao, Beijing (CN); Huimin Hu, Beijing (CN); He Zhao, Beijing (CN)

(73) Assignee: CHINA NATIONAL INSTITUTE OF STANDARDIZATION, Beijing (CN)

( * ) Notice: Subject to any disclaimer, the term of this patent is extended or adjusted under 35 U.S.C. 154(b) by 0 days.

(21) Appl. No.: 17/764,206

(22) PCT Filed: Mar. 16, 2021

(86) PCT No.: PCT/CN2021/080983
§ 371 (c)(1),
(2) Date: Mar. 28, 2022

(87) PCT Pub. No.: WO2022/110573
PCT Pub. Date: Jun. 2, 2022

(65) Prior Publication Data
US 2022/0378329 A1 Dec. 1, 2022

(30) Foreign Application Priority Data
Nov. 24, 2020 (CN) .......................... 202011325500.4

(51) Int. Cl.
*A61B 5/11* (2006.01)
*A61B 5/00* (2006.01)

(52) U.S. Cl.
CPC .......... *A61B 5/1121* (2013.01); *A61B 5/1127* (2013.01); *A61B 5/1128* (2013.01); *A61B 5/7271* (2013.01)

(58) Field of Classification Search
CPC ... A61B 5/1121; A61B 5/1127; A61B 5/1128; A61B 5/4576
See application file for complete search history.

(56) References Cited

U.S. PATENT DOCUMENTS 11,024,053 B1 * 6/2021 Zhang ........................ G06T 5/20
2007/0213643 A1 * 9/2007 Gotte ................... A61B 5/4528
600/595

(Continued)

FOREIGN PATENT DOCUMENTS

CA 2595167 A1 1/2008
CN 1466439 A 1/2004

(Continued)

OTHER PUBLICATIONS

Veeger et al., The position of the rotation center of the glenohumeral joint, Journal of Biomechanics 33 (2000) 1711}1715 (Year: 2000).*

(Continued)

*Primary Examiner* — Jacqueline Cheng
*Assistant Examiner* — Tho Q Tran
(74) *Attorney, Agent, or Firm* — Bayramoglu Law Offices LLC

(57) ABSTRACT

A positioning method of functional rotation center of shoulder based on rigid upper arm model includes: step 1: abstracting a human upper arm into a cylinder with FRCS as a center of top surface; step 2: determining a reference axis vector of the cylinder; step 3: determining an axis vector of the cylinder and a displacement from the reference axis vector to the axis vector; step 4: correcting a central axis direction of the cylinder; step 5: determining a height (Continued)

compensation of the cylinder, and positioning the FRCS. The method has higher accuracy for the positioning result of FRCS, the positioning result of FRCS has better stability relative to the upper arm and trunk, and can be used to establish a more accurate human digital dynamic model and predict more accurate human posture.

9 Claims, 18 Drawing Sheets

(56) References Cited

U.S. PATENT DOCUMENTS

| | | | | |
|---|---|---|---|---|
| 2009/0322763 | A1* | 12/2009 | Bang | G06V 40/23 |
| | | | | 73/865.4 |
| 2016/0324461 | A1 | 11/2016 | Hallberg | |
| 2022/0125519 | A1* | 4/2022 | Slagmolen | A61B 90/36 |

FOREIGN PATENT DOCUMENTS

| | | |
|---|---|---|
| CN | 1748642 A | 3/2006 |
| CN | 107802268 A | 3/2018 |
| CN | 107923741 A | 4/2018 |
| CN | 108013880 A | 5/2018 |
| CN | 108030496 A | 5/2018 |
| CN | 108324282 A | 7/2018 |
| DE | 102007031946 A1 | 1/2009 |
| EP | 2773290 A1 | 9/2014 |
| JP | 2005245476 A | 9/2005 |
| WO | 2004097746 A1 | 11/2004 |

OTHER PUBLICATIONS

Lempereur et al., In vivo estimation of the glenohumeral joint centre by functional methods: Accuracy and repeatability assessment, Journal of Biomechanics 43 (2010) 370-374 (Year: 2010).*

Liu Zhen-Yu, et al., Estimation for Rotated Center of Shoulder in Human Upper Limb Dynamic Motion Measurement, Journal of Tianjin University of Science &Technology, 2007, pp. 55-58, vol. 22, No. 1.

Zhang Jianguo, et al., Application of Double-Coordinate System on Motion Measurement of Human Upper-Limb, Computer Measurement & Control, 2007, pp. 1308-1311, vol. 15, No. 10.

Huang Hai-Ming, et al., A Kind of Precise and Efficient Algorithm on Judging the Center of Joint Rotation, Journal of System Simulation, 2005, pp. 815-521, vol. 17, No. 4.

Kei Aoki, et al., A Kinematic Estimation of Functional Joint Rotation Centers of Whole Body, Digital Human Technology Consortium Japan, 2014.

M. Crabolu, et al., In vivo estimation of the shoulder joint center of rotation using magneto-inertial sensors: MRI-based accuracy and repeatability assessment, BioMedical Engineering OnLine, 2017, pp. 1-18, vol. 16., No. 34.

* cited by examiner

POSITIONING METHOD OF FUNCTIONAL ROTATION CENTER OF SHOULDER BASED ON RIGID UPPER ARM MODEL

CROSS REFERENCE TO THE RELATED APPLICATIONS

This application is the national phase entry of International Application No. PCT/CN2021/080983, filed on Mar. 16, 2021, which is based upon and claims priority to Chinese Patent Application No. 202011325500.4, filed on Nov. 24, 2020, the entire contents of which are incorporated herein by reference.

TECHNICAL FIELD

The present invention relates to the technical field of human motion measurement, in particular to a positioning method of functional rotation center of shoulder based on rigid upper arm model.

BACKGROUND

At present, human motion measurement and posture prediction technology are playing an important role in various fields, such as athlete selection, motion capture of sports, computer vision, biomedicine and medical devices. In process of human motion measurement and posture prediction, shoulder joint is the most flexible joint in human upper limb, and its positioning is an important link in establishing human digital dynamic model.

In field of biomedicine, glenohumeral anatomical center (GHAC) infers from a position of a humeral head in anatomy; in field of human motion measurement, the functional rotation center of shoulder (FRCS) is defined as a rotation center of an upper arm in motion, and is positioned by kinematic parameters of the human upper arm.

Before concept of the FRCS is put forward, the positioning of the rotation center of the shoulder joint uses a method of locating the GHAC for reference, that is, according to scanning results of human shoulder contour and combining with complex anatomical knowledge, the bone shape envelope of humerus and scapula is predicted and researched digitally, so as to locate the rotation center of the shoulder joint. However, because the measurement of the GHAC is completed under static or approximate static conditions, even if the bone shape envelope of humerus and scapula is estimated very accurately, the rotation center of the shoulder joint positioned is still very insufficient in establishing the human digital dynamic model.

After the concept of the FRCS is put forward, early FRCS is located by using a cadaver, an intersection of three rotation axes, FRCS, is located by setting long nails on the rotation axes of the upper arm of the cadaver. However, because the movement of the cadaver is non-subjective, the FRCS determined by this method still has defect of insufficient accuracy in establishing the human digital dynamic model.

Japan Digital Human Research Center proposes a method to measure human FRCS in motion, the method completely abandons restriction of anatomical knowledge on the FRCS, and obtains accurate reachable domain of the upper limb by using geometric algorithm. Advantages of this method are the FRCS is calculated according to a moving human body and is more in accord with motion posture of the human body, and there is a correlation between the position of the FRCS of the moving human body and limb angle, which can be used to establish a more accurate human digital dynamic model. In the case of losing a geometric limitation of the anatomical knowledge, a positioning error of the FCRS caused by systematic error, skin deformation and so on will be transmitted and amplified in geometric calculation, resulting in serious deviation of FRCS positioning result.

SUMMARY

In order to solve the problem of insufficient accuracy of the FRCS positioning result in the above prior art, the present invention provides a positioning method of functional rotation center of shoulder based on rigid upper arm model.

A positioning method of functional rotation center of shoulder based on rigid upper arm model, comprises:
- step 1: abstracting a human upper arm into a cylinder with FRCS as a center of top surface;
- step 2: determining a reference axis vector of the cylinder;
- step 3: determining an axis vector of the cylinder and a displacement from the reference axis vector to the axis vector;
- step 4: correcting a central axis direction of the cylinder;
- step 5: determining a height compensation of the cylinder, and positioning the FRCS.

Preferably, in the step 1, skin surface of the human upper arm is abstracted as side surface of the cylinder.

In any of the above solutions, it is preferred that in the step 2, the reference axis vector is a vector $\overrightarrow{A^{rm}}$ which starts from a midpoint (represented by mark MD) of medial and lateral epicondylar points of the humerus on human surface and points to an acromion point (represented by mark MU), and its direction is a reference direction of the cylinder.

In any of the above solutions, it is preferred that in the step 2, $\overrightarrow{A^{rm}} = M^U - M^D$, wherein $M^U = [X^U\ Y^U\ Z^U]^T$ represents position information of the acromion point MU, $M^D = [X^D\ Y^D\ Z^D]^T$ represents position information of the midpoint MD of the medial and lateral epicondylar points of the humerus;

In any of the above solutions, it is preferred that for any point A on the skin surface of the human upper arm, position information of the point A from starting time $t_0$ to ending time $t_S$ is expressed as $M^A$, $$M^A = [X^A\ Y^A\ Z^A]^T = \begin{bmatrix} X^A_{t_0} & X^A_{t_0+\Delta t} & X^A_{t_0+2\Delta t} & \cdots & X^A_{t_s} \\ Y^A_{t_0} & Y^A_{t_0+\Delta t} & Y^A_{t_0+2\Delta t} & \cdots & Y^A_{t_s} \\ Z^A_{t_0} & Z^A_{t_0+\Delta t} & Z^A_{t_0+2\Delta t} & \cdots & Z^A_{t_s} \end{bmatrix},$$

wherein $t_s = t_0 + k\Delta t$, $k \geq 3$, $\Delta t$ is sampling interval.

In any of the above solutions, it is preferred that in the step 3, the reference axis vector is translated $\overrightarrow{D^{pm}}$ in a direction perpendicular to the reference direction to obtain the axis vector, and the distance from the axis vector to each point on the skin surface of the upper arm is equal.

In any of the above solutions, it is preferred that an end point of the axis vector is a vertex of the cylinder, that is, FRCS, and position information of the FRCS is expressed as:

$$RCS^F = M^U + \overrightarrow{D^{pm}} \tag{①}.$$

In any of the above solutions, it is preferred that the step 3 comprises:
- step 31: determining three marking points M1, M2 and M3 on the skin surface of the human upper arm, and vertical vectors $\vec{R^1}$, $\vec{R^2}$, and $\vec{R^3}$ respectively from the marking points M1, M2 and M3 to the reference axis vector being translated to make a start point of each vertical vector be located at the midpoint MD of the medial and lateral epicondylar points of the humerus at that time;

step 32: determining a center of a circle where an end point of each vertical vector is located after translation (represented by mark O), a displacement from the midpoint MD of the medial and lateral epicondyle points of the humerus to the center O being a displacement from the reference axis vector to the axis vector, namely $\vec{D^{pm}}$.

In any of the above solutions, it is preferred that in the step 3, for any time $t_a$ in process, translating a coordinate system to establish a local coordinate system which takes $M_{t_a}^D = [X_{t_a}^D \ Y_{t_a}^D \ Z_{t_a}^D]^T$ as a coordinate origin, then, at the time $t_a$, reverse vectors $\vec{R_{t_a}^n}$ of vertical vectors respectively from the marking points M1, M2 and M3 to the reference axis vector satisfy a relational formula $\vec{R_{t_a}^n} = R_{t_a}^n - 0$, wherein, $R_{t_a}^n$ represent end coordinates of the vectors $\vec{R_{t_a}^n}$, n=1, 2, 3.

In any of the above solutions, it is preferred that according to formula $$\begin{vmatrix} O_{xt_a} & O_{yt_a} & O_{zt_a} & 1 \\ R_{xt_a}^1 & R_{yt_a}^1 & R_{zt_a}^1 & 1 \\ R_{xt_a}^2 & R_{yt_a}^2 & R_{zt_a}^2 & 1 \\ R_{xt_a}^3 & R_{yt_a}^3 & R_{zt_a}^3 & 1 \end{vmatrix} = 0 \quad (4)$$

and formula $$(R_{xt_a}^1 - O_{xt_a})^2 + (R_{yt_a}^1 - O_{yt_a})^2 + (R_{zt_a}^1 - O_{zt_a})^2 =$$
$$(R_{xt_a}^2 - O_{xt_a})^2 + (R_{yt_a}^2 - O_{yt_a})^2 + (R_{zt_a}^2 - O_{zt_a})^2 = \quad (5)$$
$$(R_{xt_a}^3 - O_{xt_a})^2 + (R_{yt_a}^3 - O_{yt_a})^2 + (R_{zt_a}^3 - O_{zt_a})^2$$

determine coordinates $O_{t_a} = [O_{xt_a}, O_{yt_a}, O_{zt_a}]^T$ of the center O at the time $t_a$, restore them to a global coordinate system, that is, translate the vector $\vec{A^{rm}}$ to make a starting point of the vector $A^{rm}$ coincide with the $O_{t_a}$ to obtain a translation $\vec{D^{pm}}$, at this time, an end point of the vector $\vec{A^{rm}}$ after translation is the position of the FRCS.

In any of the above solutions, it is preferred that in the step 4, the central axis of the cylinder is corrected by introducing a proportion coefficient n of a height of the marking point on the surface of the upper arm in the cylinder to a total height of the cylinder.

In any of the above solutions, it is preferred that the step 4 includes:

step 41: projecting the three marking points M1, M2 and M3 on the surface of the upper arm to the reference axis vector, for any time $t_a$ in the process, there being relational formulas $$\begin{cases} n_{t_a}^{fir} \vec{A_{t_a}^{rm}} + \vec{R_{t_a}^1} = M_{t_a}^1 - M_{t_a}^D \\ n_{t_a}^{sec} \vec{A_{t_a}^{rm}} + \vec{R_{t_a}^2} = M_{t_a}^2 - M_{t_a}^D \\ n_{t_a}^{thd} \vec{A_{t_a}^{rm}} + \vec{R_{t_a}^1} = M_{t_a}^3 - M_{t_a}^D \end{cases} \quad (6)$$

and $$\begin{cases} \vec{A_{t_a}^{rm}} \cdot \vec{R_{t_a}^1} = 0 \\ \vec{A_{t_a}^{rm}} \cdot \vec{R_{t_a}^2} = 0 \\ \vec{A_{t_a}^{rm}} \cdot \vec{R_{t_a}^3} = 0 \end{cases} \quad (7)$$

wherein $\vec{R_{t_a}^1}$ represents a vector starting from a perpendicular foot from the marking point M1 to the vector $\vec{A_{t_a}^{rm}}$ and pointing to the marking point M1 at time $t_a$, meanings of $\vec{R_{t_a}^2}$ and $\vec{R_{t_a}^3}$ can be inferred from this; $n_{t_a}^{fir}$, $n_{t_a}^{sec}$ and $n_{t_a}^{thd}$ respectively represent ratios of vectors starting from MD and pointing to the perpendicular foot of the marking points M1, M2 and M3 to the vector $\vec{A_{t_a}^{rm}}$ at the time $t_a$; $M_{t_a}^1$ represents position coordinates of the marking point M1 at the time $t_a$, meanings of $M_{t_a}^2$, $M_{t_a}^3$, $M_{t_a}^D$, $M_{t_a}^U$ can be inferred from this.

step 42: marking $n^{fir} = [n_{t_0}^{fir} \ n_{t_0 + \Delta t}^{fir} \ n_{t_0 \circ 2\Delta t}^{fir} \ldots n_{t_S}^{fir}]$, $$n^{al} = \begin{bmatrix} n^{fir} \\ n^{sec} \\ n^{thd} \end{bmatrix},$$

combining formula $\hat{6}$ with formula $\hat{7}$, obtaining that at the time $t_a$:

$$n_{t_a}^{al} = \begin{bmatrix} (M_{t_a}^1 - M_{t_a}^D)^T \\ (M_{t_a}^2 - M_{t_a}^D)^T \\ (M_{t_a}^3 - M_{t_a}^D)^T \end{bmatrix} \cdot (M_{t_a}^U - M_{t_a}^D) \cdot ((M_{t_a}^U - M_{t_a}^D)^T \cdot (M_{t_a}^U - M_{t_a}^D))^{-1}.$$

step 43: selecting a proportion coefficient $n_{t_j}^{al}$ as a standard coefficient at time $t_j$ when arms are vertically downward in a human standing posture, adding a correction amount $\vec{A_{ta}^{cps}}$ to the $\vec{A_{ta}^{rm}}$ at any time $t_a$ to make the proportion coefficient $n_{t_a}^{al}$ close to $n_{t_j}^{al}$, that is to make:

$$n^{al'} = \begin{bmatrix} n_{t_j}^{fir} \cdot [1 \ 1 \ \ldots \ 1] \\ n_{t_j}^{sec} \cdot [1 \ 1 \ \ldots \ 1] \\ n_{t_j}^{thd} \cdot [1 \ 1 \ \ldots \ 1] \end{bmatrix}$$

and $n^{al'}$ and $\vec{A_{t_a}^{rm'}}$ after corrected meet the requirements of the formulas ④ and ⑤.

step 44: according to the correction amount $\vec{A_{ta}^{cps}}$ change modulus $|\vec{A_{t_a}^{rm}}|$ of the axis vector, obtaining:

$$|\vec{A_{t_a}^{rm'}}| = |\vec{A_{t_a}^{rm}} + \vec{A_{t_a}^{cps}}| = |\vec{A_{t_a}^{rm}}| \quad (8)$$

step 45: in a conical generatrix set satisfying the first column of formula ⑥, the first column of formula ⑦ and formula ⑧, a conical generatrix set satisfying the second column of formula ⑥, the second column of formula ⑦ and formula ⑧, and the conical generatrix set satisfying the third column of formula ⑥, the third column of formula ⑦ and formula ⑧, respectively selecting solutions closest to $\vec{A_{t_a}^{rm}}$ and combining them to obtain $\overrightarrow{A_{t_a}^{rm'}}$, and then obtaining a final correction $\overrightarrow{A_{ta}^{cps}}$, according to the final correction $\overrightarrow{A_{ta}^{cps}}$, rewriting the formula ① as:

$$RCS^F = M^U + \overrightarrow{A^{cps}} + \overrightarrow{D^{pm}} \qquad (13)$$

wherein $\overrightarrow{D^{pm}}$ is resolved according to the axis vector $\overrightarrow{A^{rm'}}$ in the correction direction.

In any of the above solutions, it is preferred that in the step 5, after determine the height compensation of the cylinder, a final calculation formula of FRCS is:

$$RCS^F = M^U + \overrightarrow{A^{cps}} + \overrightarrow{D^{pm}} - (1 - l^{rm})(\overrightarrow{A^{rm}} + \overrightarrow{A^{cps}}) \qquad (17)$$

wherein, the $l^{rm}$ is a height compensation coefficient of the cylinder.

The positioning method of functional rotation center of shoulder based on rigid upper arm model of the present invention has higher accuracy for the positioning result of FRCS, the positioning result of FRCS has better stability relative to the upper arm and trunk, and can be used to establish a more accurate human digital dynamic model and predict more accurate human posture.

DETAILED DESCRIPTION OF THE EMBODIMENTS

For better understanding of the present invention, detailed description of the invention is provided below with reference to specific embodiments.

Embodiment 1

Figure 1:
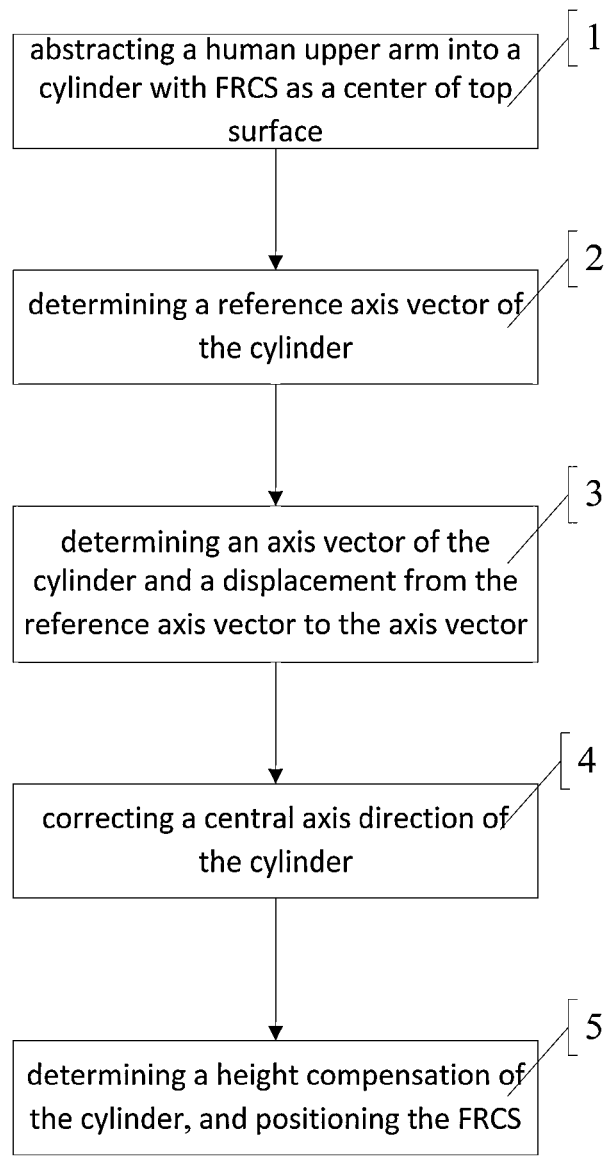
FIG. 1 is a flowchart of a preferred embodiment of a positioning method of functional rotation center of shoulder based on rigid upper arm model according to the present invention.

As shown in FIG. 1, a positioning method of functional rotation center of shoulder based on rigid upper arm model comprises:
- step 1: abstracting a human upper arm into a cylinder with FRCS as a center of top surface;
- step 2: determining a reference axis vector of the cylinder;
- step 3: determining an axis vector of the cylinder and a displacement from the reference axis vector to the axis vector;
- step 4: correcting a central axis direction of the cylinder;
- step 5: determining a height compensation of the cylinder, and positioning the FRCS.

For the step 1: abstracting a human upper arm into a cylinder with FRCS as a center of top surface, in this embodiment:

when human trunk is fixed, a main way of movement of the upper arm is rotation. In a very short time, motion amplitude of an end of a humerus is much greater than that of a top of the humerus, if a deformation of the upper arm in the movement is ignored, the upper arm rotates approximately around the FRCS in the movement. In geometric operations, if spatial position changes of at least three points on surface of the upper arm can be obtained, a position of the FRCS can be determined. Therefore, in the step 1, the human upper arm is abstracted into a cylinder with FRCS as a center of top surface, and accordingly, the skin surface of the human upper arm is abstracted as side surface of the cylinder.

Figure 2:
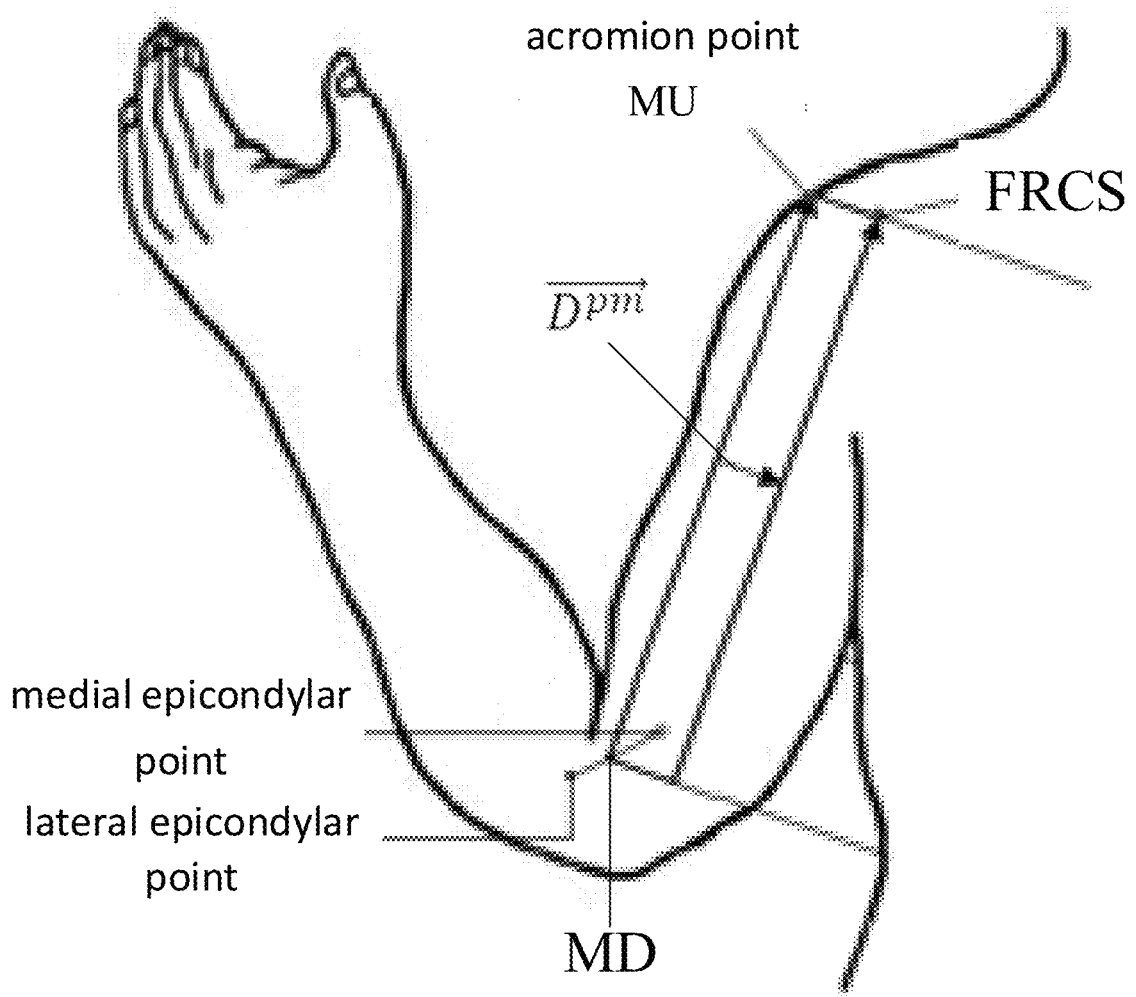
FIG. 2 is a schematic diagram of a reference axis vector and an axis vector of the embodiment shown in FIG. 1 of positioning method of functional rotation center of shoulder based on rigid upper arm model according to the present invention.

For the step 2: determining a reference axis vector of the cylinder, in this embodiment:

as shown in FIG. 2, in the step 2, the reference axis vector is a vector $\overrightarrow{A^{rm}}$ which starts from a midpoint (represented by mark MD) of medial and lateral epicondylar points of the humerus on human surface and points to an acromion point (represented by mark MU), and its direction is a reference direction of the cylinder, mark $\overrightarrow{A^{rm}} = M^U - M^D$, wherein $M^D = [X^U \ Y^U \ Z^U]^T$ represents position information of the acromion point MU, $M^D = [X^D \ Y^D \ Z^D]^T$ represents position information of the midpoint MD of the medial and lateral epicondylar points of the humerus.

In motion measurement, a measurement process will last for a period, for convenience of description, starting time of the measurement process is denoted by $t_0$, and ending time thereof is denoted by $t_S$, during the period, positions of selected marking points on human surface are continuously collected to obtain position information of the marking points on the human surface within the period. For any point A on the skin surface of the human upper arm, position information of the point A from starting time $t_0$ to ending time $t_S$ is expressed as $M^A$, $$M^A = [X^A \ Y^A \ Z^A]^T = \begin{bmatrix} X^A_{t_0} & X^A_{t_0+\Delta t} & X^A_{t_0+2\Delta t} & \cdots & X^A_{t_S} \\ Y^A_{t_0} & Y^A_{t_0+\Delta t} & Y^A_{t_0+2\Delta t} & \cdots & Y^A_{t_S} \\ Z^A_{t_0} & Z^A_{t_0+\Delta t} & Z^A_{t_0+2\Delta t} & \cdots & Z^A_{t_S} \end{bmatrix},$$

wherein $t_S = t_0 + k\Delta t$, $k \geq 3$, $\Delta t$ is sampling interval. In this embodiment, considering convenience of calculation, limitation of experimental conditions, and accuracy and repeatability of calculation results, it is set that $k=500$, $\Delta t = 0.01$ ms.

For the step 3: determining an axis vector of the cylinder and a displacement from the reference axis vector to the axis vector, in this embodiment:

as shown in FIG. 2, in the step 3, the reference axis vector $\overrightarrow{A^{rm}}$ is translated $\overrightarrow{D^{pm}}$ in a direction perpendicular to the reference direction to obtain the axis vector, and distance from the axis vector to each point on the skin surface of the upper arm is equal. An end point of the axis vector is a vertex of the cylinder, that is, FRCS, and position information of the FRCS is expressed as:

$$RCS^F = M^U + \overrightarrow{D^{pm}} \quad \text{(①)}.$$

Figure 3:
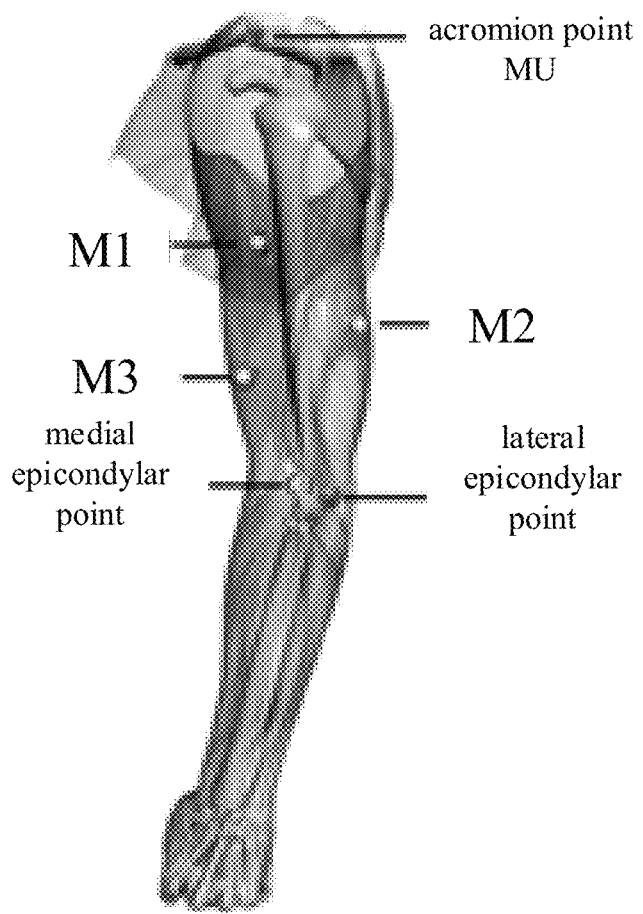
FIG. 3 is a schematic diagram of three marking points of the embodiment shown in FIG. 1 of the positioning method of functional rotation center of shoulder based on rigid upper arm model according to the present invention.

Because the axis vector is obtained by translating the reference axis vector in the direction perpendicular to the reference direction, and the distance from the axis vector to the marking points on the upper arm is equal, therefore, if three mark points are selected on skin surface of the upper arm, according to properties in spatial geometry that a section of the cylinder is circular, in the section of the cylinder, a center of a circle formed by projection points which are obtained by projecting the three marking points on the upper arm to the section along the reference direction is an intersection of the axis vector and the mentioned section. Based on the above theory, in the step 3, a specific process of determining the displacement $\overrightarrow{D^{pm}}$ from the reference axis vector to the axis vector comprises:

step 31: as shown in FIG. 3, determining three marking points M1, M2 and M3 on the skin surface of the human upper arm, and vertical vectors $\overrightarrow{R^1}$, $\overrightarrow{R^2}$, and $\overrightarrow{R^3}$ respectively from the marking points M1, M2 and M3 to the reference axis vector being translated to make a start point of each vertical vector be located at the midpoint MD of the medial and lateral epicondylar points of the humerus at that time;

step 32: determining a center of a circle where an end point of each vertical vector is located after translation (represented by mark O), a displacement from the midpoint MD of the medial and lateral epicondyle points of the humerus to the center O being a displacement from the reference axis vector to the axis vector, namely $\overrightarrow{D^{pm}}$.

Specifically, for any time $t_a$ in the measurement process, translating a coordinate system to establish a local coordinate system which takes $M_{t_a}^D = [X_{t_a}^D \ Y_{t_a}^D \ Z_{t_a}^D]^T$ as a coordinate origin, then, at the time $t_a$, reverse vectors $\overrightarrow{E_{t_a}^n}$ of vertical vectors respectively from the marking points M1, M2 and M3 to the reference axis vector satisfy a relational formula $\overrightarrow{R_{t_a}^n} = R_{t_a}^n - 0$, wherein, $R_{t_a}^n$ represent end coordinates of the vectors $\overrightarrow{R_{t_a}^n}$, $n=1, 2, 3$. In a plane where three points represented by coordinates $R_{t_a}^1$, $R_{t_a}^2$ and $R_{t_a}^3$ are located, find a center of a circle where the three points are located on: since the three points and the center of the circle where the three points are located on are in the same plane, then:

$$\begin{vmatrix} O_{xt_a} & O_{yt_a} & O_{zt_a} & 1 \\ R^1_{xt_a} & R^1_{yt_a} & R^1_{zt_a} & 1 \\ R^2_{xt_a} & R^2_{yt_a} & R^2_{zt_a} & 1 \\ R^3_{xt_a} & R^3_{yt_a} & R^3_{zt_a} & 1 \end{vmatrix} = 0, \quad \text{(④)}$$

at the same time, because the distances from the three points to the center of the circle where the three points are located on are equal, then:

$$(R^1_{xt_a} - O_{xt_a})^2 + (R^1_{yt_a} - O_{yt_a})^2 + (R^1_{zt_a} - O_{zt_a})^2 = \quad \text{(⑤)}$$
$$(R^2_{xt_a} - O_{xt_a})^2 + (R^2_{yt_a} - O_{yt_a})^2 + (R^2_{zt_a} - O_{zt_a})^2 =$$
$$(R^3_{xt_a} - O_{xt_a})^2 + (R^3_{yt_a} - O_{yt_a})^2 + (R^3_{zt_a} - O_{zt_a})^2,$$

combining formula ④ with formula ⑤, coordinates $O_{t_a} = [O_{xt_a} \ O_{yt_a} \ O_{zt_a}]^T$ of center O at the time $t_a$ can be determined, and then restore them to a global coordinate system, that is, translate the vector $\overrightarrow{A^{rm}}$ to make a starting point of the vector $\overrightarrow{A^{rm}}$ coincide with the $O_{t_a}$ to obtain a translation $\overrightarrow{D^{pm}}$, at this time, an end point of the vector $\overrightarrow{A^{rm}}$ after translation is the position of the FRCS For the step 4: correcting a central axis direction of the cylinder, in this embodiment: the reference axis vector $\overrightarrow{A^{rm}}$ is determined according to a bony landmarks point, geometrically, it deviates from the central axis of the cylinder (the line where the axis vector is located), in order to make the calculation results more accurate, a direction of the central axis of the cylinder needs to be corrected.

A rigid cylinder does not be deformed in translation and rotation, so a relative position of points on its surface in the cylinder is unchanged, and then a cutting ratio of an intersection of a cross section where the points on its surface are located and the central axis to a central axis segment is unchanged. The central axis of the cylinder is corrected by introducing a proportion coefficient n of a height of marking point on the surface of the upper arm in the cylinder to a total height of the cylinder.

Figure 4:
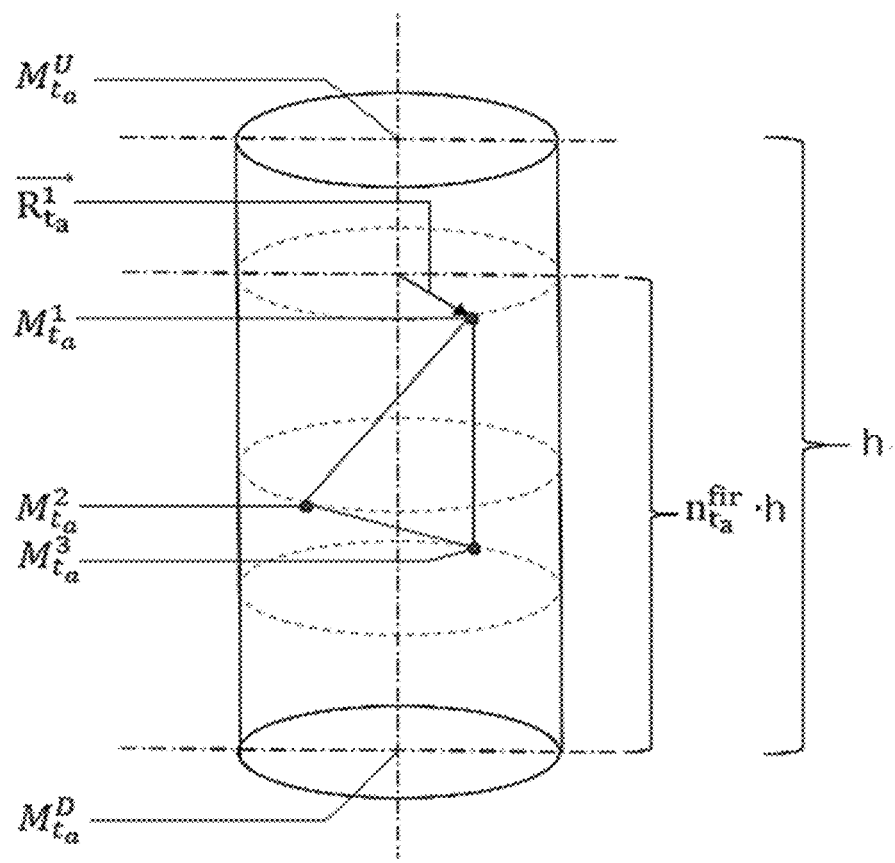
FIG. 4-FIG. 6 are schematic diagrams of correction of a central axis of the embodiment shown in FIG. 1 of the positioning method of functional rotation center of shoulder based on rigid upper arm model according to the present invention.

As shown in FIG. 4, the step 4 comprises:

step 41: projecting the three marking points M1, M2 and M3 on the surface of the upper arm to the reference axis vector, for any time $t_a$ in the process, there being relational formulas $$\begin{cases} n_{t_a}^{fir} \overrightarrow{A_{t_a}^{rm}} + \overrightarrow{R_{t_a}^1} = M_{t_a}^1 - M_{t_a}^D \\ n_{t_a}^{sec} \overrightarrow{A_{t_a}^{rm}} + \overrightarrow{R_{t_a}^2} = M_{t_a}^2 - M_{t_a}^D \\ n_{t_a}^{thd} \overrightarrow{A_{t_a}^{rm}} + \overrightarrow{R_{t_a}^1} = M_{t_a}^3 - M_{t_a}^D \end{cases} \quad (6)$$

and $$\begin{cases} \overrightarrow{A_{t_a}^{rm}} \cdot \overrightarrow{R_{t_a}^1} = 0 \\ \overrightarrow{A_{t_a}^{rm}} \cdot \overrightarrow{R_{t_a}^2} = 0 \\ \overrightarrow{A_{t_a}^{rm}} \cdot \overrightarrow{R_{t_a}^3} = 0 \end{cases} \quad (7)$$

wherein $\overrightarrow{R_{t_a}^1}$ represents a vector starting from a perpendicular foot from the marking point M1 to the vector $\overrightarrow{A_{t_a}^{rm}}$ and pointing to the marking point M1 at time $t_a$, meanings of $\overrightarrow{R_{t_a}^2}$ and $\overrightarrow{R_{t_a}^3}$ can be inferred from this; $n_{t_a}^{fir}$, $n_{t_a}^{sec}$ and $n_{t_a}^{thd}$ respectively represent ratios of vectors starting from MD and pointing to the perpendicular foot of the marking points M1, M2 and M3 to the vector $\overrightarrow{A_{t_a}^{rm}}$ at the time $t_a$; $M_{t_a}^1$ represents position coordinates of the marking point M1 at the time $t_a$, meanings of $M_{t_a}^2$, $M_{t_a}^3$, $M_{t_a}^D$, $M_{t_a}^U$ can be inferred from this.

step 42: marking $n^{fir}=[n_{t_0}^{fir} \ n_{t_0+\Delta t}^{fir} \ N_{t_0+2\Delta t}^{fir} \ \ldots \ n_{t_S}^{fir}]$, $$n^{al} = \begin{bmatrix} n^{fir} \\ n^{sec} \\ n^{thd} \end{bmatrix},$$

combining formula (6) with formula (7), and obtaining that at the time $t_a$:

$$n_{t_a}^{al} = \begin{bmatrix} (M_{t_a}^1 - M_{t_a}^D)^T \\ (M_{t_a}^2 - M_{t_a}^D)^T \\ (M_{t_a}^3 - M_{t_a}^D)^T \end{bmatrix} \cdot (M_{t_a}^U - M_{t_a}^D) \cdot ((M_{t_a}^U - M_{t_a}^D)^T \cdot (M_{t_a}^U - M_{t_a}^D))^{-1}.$$

step 43: the proportion coefficient n is used to describe a proportion of the height of the marking point in the cylinder to the total height of the cylinder, in the rigid cylinder, the coefficient n corresponding to the same marking point does not change during movement of the cylinder. However, since $\overrightarrow{A^{rm}}$ is not parallel to the actual central axis, during the whole test period $(t_S-t_0)$, the coefficients n of the same marking point at different times are not all the same, so that, a proportion coefficient $n_{t_j}^{al}$ at time $t_j$ when the arms are vertically downward in a human standing posture being selected as a standard coefficient, adding a correction amount $\overrightarrow{A_{ta}^{cps}}$ to the $\overrightarrow{A_{t_1}^{rm}}$ at any time $t_1$ to make the proportion coefficient $n_{t_j}^{al'}$ close to $n_{t_j}^{al}$, that is to make:

$$n^{al'} = \begin{bmatrix} n_{t_j}^{fir} \cdot [1 \ 1 \ \ldots \ 1] \\ n_{t_j}^{sec} \cdot [1 \ 1 \ \ldots \ 1] \\ n_{t_j}^{thd} \cdot [1 \ 1 \ \ldots \ 1] \end{bmatrix}$$

and $n^{al'}$ and $\overrightarrow{A_{t_a}^{rm'}}$ after correction meet requirements of the formulas (4) and (5).

step 44: according to the correction amount $\overrightarrow{A_{ta}^{cps}}$ doesn't change modulus $|\overrightarrow{A_{t_a}^{rm}}|$ of the axis vector, obtaining:

$$|\overrightarrow{A_{t_a}^{rm'}}| = |\overrightarrow{A_{t_a}^{rm}} + \overrightarrow{A_{t_a}^{cps}}| = |\overrightarrow{A_{t_a}^{rm}}| \quad (8).$$

step 45: in a conical generatrix set satisfying the first column of formula (6), the first column of formula (7) and formula (8), a conical generatrix set satisfying the second column of formula (6), the second column of formula (7) and formula (8), and a conical generatrix set satisfying the third column of formula (6), the third column of formula (7) and formula (8), respectively selecting solutions closest to $\overrightarrow{A_{t_a}^{rm}}$ and combining them to obtain $\overrightarrow{A_{t_a}^{rm'}}$, and then obtaining a final correction $\overrightarrow{A_{ta}^{cps}}$, according to the final correction $\overrightarrow{A_{ta}^{cps}}$, rewriting the formula (1) as:

$$RCS^F = M^U + \overrightarrow{A^{cps}} + \overrightarrow{D^{pm}} \quad (13)$$

wherein $\overrightarrow{D_{pm}}$ is resolved according to the axis vector $\overrightarrow{A^{rm'}}$ in the correction direction.

Figure 5A:
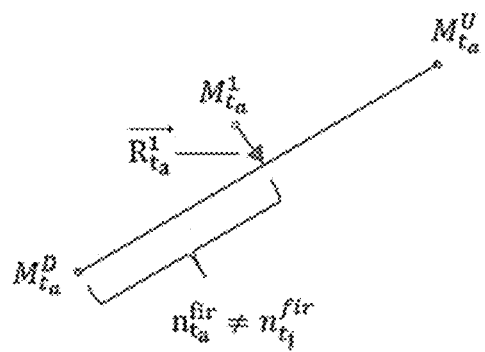
Figure 5B:
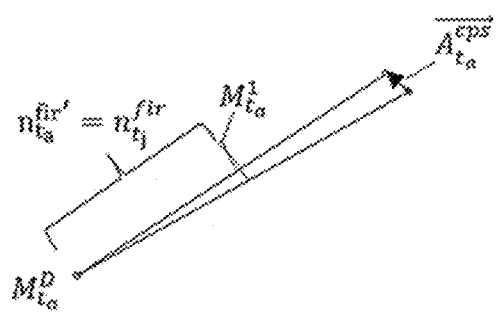
Figure 5C:
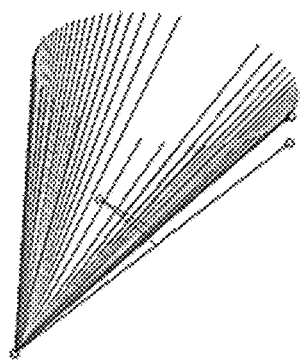
Figure 6:
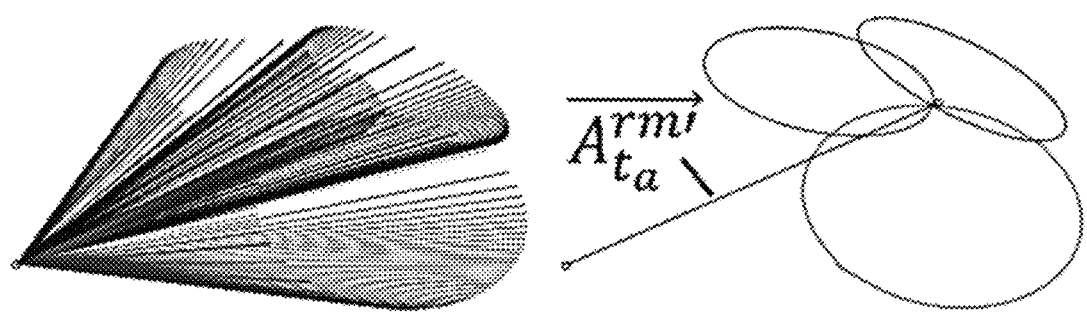

The number of the correction amount $\overrightarrow{A_{ta}^{cps}}$ satisfying the first column of formula (6), the first column of formula (7) and formula (8) is infinite, as shown in FIG. 5A, FIG. 5B, and FIG. 5C, a set of $\overrightarrow{A_{t_a}^{rm'}}$ satisfying the above condition is a conical generatrix set rotating around $(M_{t_a}^1 - M_{t_a}^D)$; similarly, a set of $\overrightarrow{A_{t_a}^{rm'}}$ satisfying the second column of formula (6), the second column of formula (7) and formula (8) is a conical generatrix set rotating around $(M_{t_a}^2 - M_{t_a}^D)$, a set of $\overrightarrow{A_{t_a}^{rm'}}$ satisfying the third column of formula (6), the third column of formula (7) and formula (8) is a conical generatrix set rotating around $(M_{t_a}^3 - M_{t_a}^D)$; therefore, as shown in FIG. 6, a simultaneous solution of the formula (6), formula (7) and formula (8) in space is a common generatrix of three cones with a same vertex. The vertices of the three cones are the same and are $M_{t_a}^D$; the central axes of the three cones are $(M_{t_a}^1 - M_{t_a}^D)$, $(M_{t_a}^2 - M_{t_a}^D)$ and $(M_{t_a}^3 - M_{t_a}^D)$ respectively; length of the generatrix of the three cones is $|\overrightarrow{A_{t_a}^{rm}}|$; perpendicular feet from the three marking points M1, M2 and M3 to their respective generatrices cut the generatrices according to the coefficient $n^{al'}$. However, in practice, there is a situation that there is no a common generatrix of three cones, that is, there is no simultaneous solution of the formula (6), formula (7) and formula (8). Therefore, in the three conical generatrix sets, solutions closest to $\overrightarrow{A_{t_a}^{rm}}$ are respectively selected and combined to obtain $\overrightarrow{A_{t_a}^{rm'}}$, and then a final correction $\overrightarrow{A_{ta}^{cps}}$ is obtained.

For the marking point M1, when vector $M_{t_a}^1 - M_{t_a}^D$ is coplanar with $\overrightarrow{A^{rm}}$ and its compensation result, there is a minimum $|\overrightarrow{A_{ta}^{cps1}}|$, setting the coefficient $n_c$ as a multiple of extending or shortening a perpendicular from the marking point to the axis to make the perpendicular intersect with the a compensated axis, then $n_c$ satisfies the formula:

$$n_{ct_a}^{fir}[n_{t_a}^{fir}\cdot\overrightarrow{A_{t_a}^{rm}} - (M_{t_a}^1 - M_{t_a}^D)] + (M_{t_a}^1 - M_{t_a}^D) = \overrightarrow{M_{t_a}^{1fits}} \quad (9)$$

wherein, $n_{ct_a}^{fir}$ is $n_c$ of the marking point M1 on the upper arm at time $t_a$, $\overrightarrow{M_{t_a}^{1fits}}$ is a vector starting from $M_{t_a}^D$ and pointing to an intersection of the perpendicular from the marking point M1 to the axis and the compensated axis. $\overrightarrow{M_{t_a}^{1fits}}$ is collinear with the compensated axis vector, and the modulus ratio between the vectors is:

$$\overrightarrow{M_{t_a}^{1fits}} \cdot |\overrightarrow{A_{t_a}^{rm}}|/|\overrightarrow{M_{t_a}^{1fits}}| = \overrightarrow{A_{t_a}^{rm}} + \overrightarrow{A_{t_a}^{cps1}} \quad (10)$$

Substitute the correction result $\overrightarrow{A_{t_a}^{rm'}} = \overrightarrow{A_{t_a}^{rm}} + \overrightarrow{A_{t_a}^{cps1}}$ into the formula ⑥, formula ⑦ and formula ⑧, then for the marking point M1 there is:

$$[(M_{t_a}^1 - M_{t_a}^D) - n_{t_j}^{fir}(\overrightarrow{A_{t_a}^{rm}} + \overrightarrow{A_{t_a}^{cps}})].*\overrightarrow{A_{t_a}^{rm}} + \overrightarrow{A_{t_a}^{cps1}} = 0 \quad (11)$$

formula ⑪ describes that the perpendicular foot from the marking points M1 to the compensated axis cuts the axis vector according to the standard coefficient $n_{t_a}^{fir}$.

When the vector $M_{t_a}^1 - M_{t_a}^D$, $\overrightarrow{A^{rm}}$ and its correction result are in a same plan, the plan intersects the cone at most twice, therefore, in the simultaneous solutions of formula ⑨, formula ⑩ and formula ⑪, there are at most two solutions of $n_c$ at the same time, a final result $n_c$ and all solutions $n_{ci}$ satisfy a formula ⑫.

$$|1 - n_c| = \min(|1 - n_{ci}|) \quad (12)$$

For the marking points M2 and M3, perform the same steps as above, and obtain the final correction amount $$\overrightarrow{A_{ta}^{cps}} : \overrightarrow{A_{ta}^{cps}} = \frac{\left(n_{ct_a}^{fir} \cdot \overrightarrow{A_{ta}^{cps1}}\right) + \left(n_{ct_a}^{sec} \cdot \overrightarrow{A_{ta}^{cps2}}\right) + \left(n_{ct_a}^{thd} \cdot \overrightarrow{A_{ta}^{cps3}}\right)}{\left(n_{ct_a}^{fir} + n_{ct_a}^{sec} + n_{ct_a}^{thd}\right)}.$$

After correction, formula ① is rewritten to obtain a calculation formula of FRCS as follows:

$$RCS^F = M^U + \overrightarrow{A^{cps}} + \overrightarrow{D^{pin}} \quad (13)$$

wherein $\overrightarrow{D^{pin}}$ is resolved according to the axis vector $\overrightarrow{A^{rm}}$ in the correction direction.

For the step 5: determining a height compensation of the cylinder and positioning the FRCS, in this embodiment:
in the step 1 to step 4, the human upper arm is abstracted into a standard rigid cylinder, but in an actual movement of the human body, a deformation of the human upper arm will cause inaccuracy of the abstraction, especially a change of a circumference of the upper arm will directly lead to a change of a radius of the cylinder, and then lead to a change of a distance from the positioning result of the FRCS to the marking point, therefore, it is necessary to compensate the positioning result of the FRCS.

Since a distance from a point on surface of the cylinder to a center of a cylinder top is related to a radius of the cylinder and a height from the point on surface of the cylinder to the cylinder top, error of the positioning result of FRCS caused by the change of the circumference of the upper arm can be compensated by stretching a height of the cylinder. A specific compensation method is:
for the marking point M1, $D_1^{st}$ is used to represent a distance between FRCS and the marking point during the test period, $m_1$ is used to represent an expectation of the distance, $l_{t_a}^{rm1}$ is used to represent a scaling ratio of the vector $\overrightarrow{A_{t_a}^{rm}}$ at the time $t_a$, then there is:

$$m_1 = E[D_1^{st}] \quad (14)$$

$$|l_{t_a}^{rm1} \cdot \overrightarrow{A_{t_a}^{rm}} - (M_{t_a}^1 - M_{t_a}^D)| = m_1 \quad (15)$$

for the marking points M2 and M3, there are relationships shown in formulas ⑭ and ⑮.

For any time $t_a$ during the test period, a scaling ratio of the cylinder, that is, a height compensation coefficient $l_{t_a}^{rm}$ is synthesized by the scaling ratios $l_{t_a}^{rm1}$, $l_{t_a}^{rm2}$ and $l_{t_a}^{rm3}$ of the three marking points M1, M2 and M3 according to:

$$l_{t_a}^{rm} = \Sigma_{i=1}^3 l_{t_a}^{rmi} \cdot k^i / (k^1 + k^2 + k^3) \quad (16)$$

wherein, $k^1$ represents a range of the distance from the marking point M1 to FRCS during the measurement time, $k^2$ represents a range of a distance from the marking point M2 to FRCS during the measurement time, and $k^3$ represents a range of a distance from the marking point M3 to FRCS during the measurement time.

After compensation, the formula ⑬ is rewritten to obtain a final calculation formula of FRCS:

$$RCS^F = M^U + \overrightarrow{A^{cps}} + \overrightarrow{D^{pin}} - (1 - l^{rm})(\overrightarrow{A^{rm}} + \overrightarrow{A^{cps}}) \quad (17)$$

wherein, $l^{rm}$ is the height compensation coefficient of the cylinder.

Figure 7:
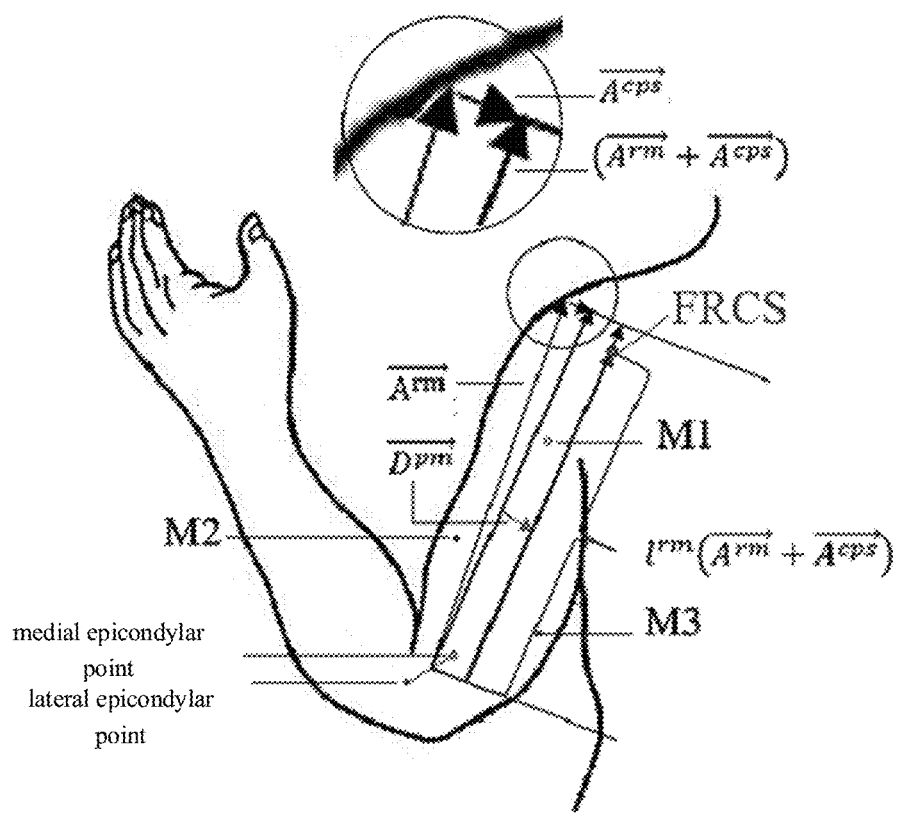
FIG. 7 is a schematic diagram of a positioning process of the embodiment shown in FIG. 1 of the positioning method of functional rotation center of shoulder based on rigid upper arm model according to the present invention.

In summary, a process of the positioning method of FRCS is shown in FIG. 7, firstly, the human upper arm is abstracted as the rigid cylinder, the reference axis vector and the axis vector of the cylinder are determined; then, the reference axis vector is corrected by adding the correction amount $\overrightarrow{A^{cps}}$, and the corrected result is $(\overrightarrow{A^{rm}} + \overrightarrow{A^{cps}})$, the translation of the reference axis vector to the axis vector $\overrightarrow{D^{pin}}$ is re-determined; and finally, the height of the cylinder is compensated, the height compensation coefficient $l^{rm}$ is determined, and the final positioning result of FRCS is obtained.

Embodiment 2

In order to verify the accuracy of the positioning method of FRCS, experiments are carried out, and the experimental results are analyzed.

Experiment

Figure 8:
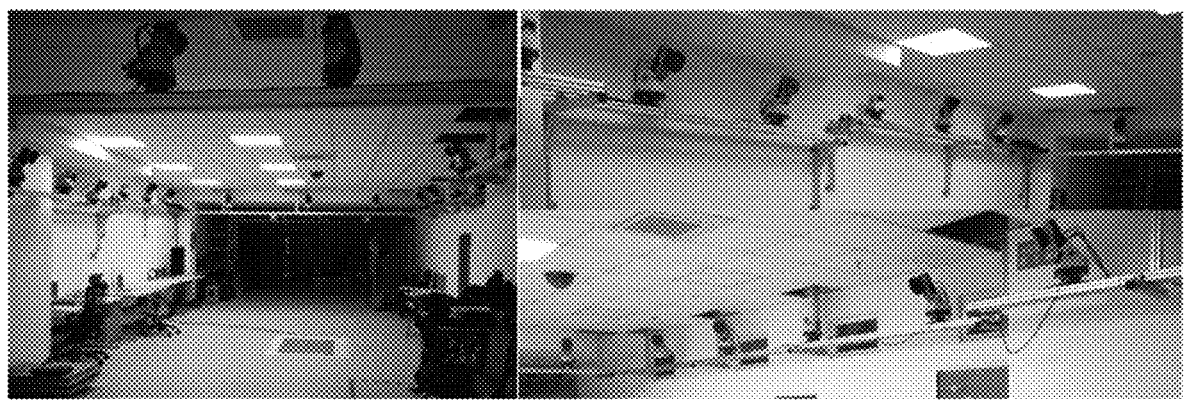
FIG. 8 is a schematic diagram of an experimental environment of another embodiment of the positioning method of functional rotation center of shoulder based on rigid upper arm model according to the present invention.

Twenty-eight adult males (18-55 years old) without upper limb dysfunction were selected as subjects to participate in the experiment, morphological parameters of the subjects are shown in Table 1. Before the experiment, all the subjects were informed of a purpose and a procedure of the experiment, and signed a consent form. In an actual measurement process, Qualisys 3D motion acquisition and analysis system was used. The system is produced by Qualisys company in Sweden and consists of motion capture camera, analysis software, acquisition unit, calibration equipment, marking ball and equipment fixing device. In the experiment, a total of 17 cameras were set, including 4 video cameras and 13 measurement cameras, the 17 cameras were evenly distributed around an experimental site, a specific distribution is shown in FIG. 8. All camera angles were adjusted to make the experimental site in centers of lens shooting ranges. A calibration accuracy of each experiment was kept below 0.7 mm.

TABLE 1

The morphological parameters of the 28 subjects

| | morphological parameter | average | maximum | minimum | variance |
|---|---|---|---|---|---|
| 1 | weight [kg] | 70.23 | 100 | 47.4 | 13.21 |
| 2 | distance to wall [mm] | 106.13 | 190 | 70 | 22.05 |
| 3 | height [mm] | 1689.40 | 1811 | 1601 | 46.96 |
| 4 | chest girth [mm] | 910.77 | 1160 | 775 | 92.06 |
| 5 | lower chest circumference [mm] | 883.07 | 1018 | 732 | 81.33 |
| 6 | right upper arm length [mm] | 318.17 | 341 | 285 | 13.89 |
| 7 | shoulder width (width between two acromion points) [mm] | 391.30 | 433 | 366 | 19.05 |
| 8 | chest width corresponding to a height of a lower chest point [mm] | 310.90 | 366 | 259 | 26.09 |
| 9 | chest thickness-chest width corresponding to a height of a midpoint of the chest [mm] | 221.30 | 259 | 186 | 21.42 |
| 10 | chest depth-a thickness at the lower chest point [mm] | 232.33 | 292 | 164 | 29.85 |
| 11 | distance form forearm to fingertip [mm] | 453.53 | 482 | 428 | 14.84 |

Figure 9:
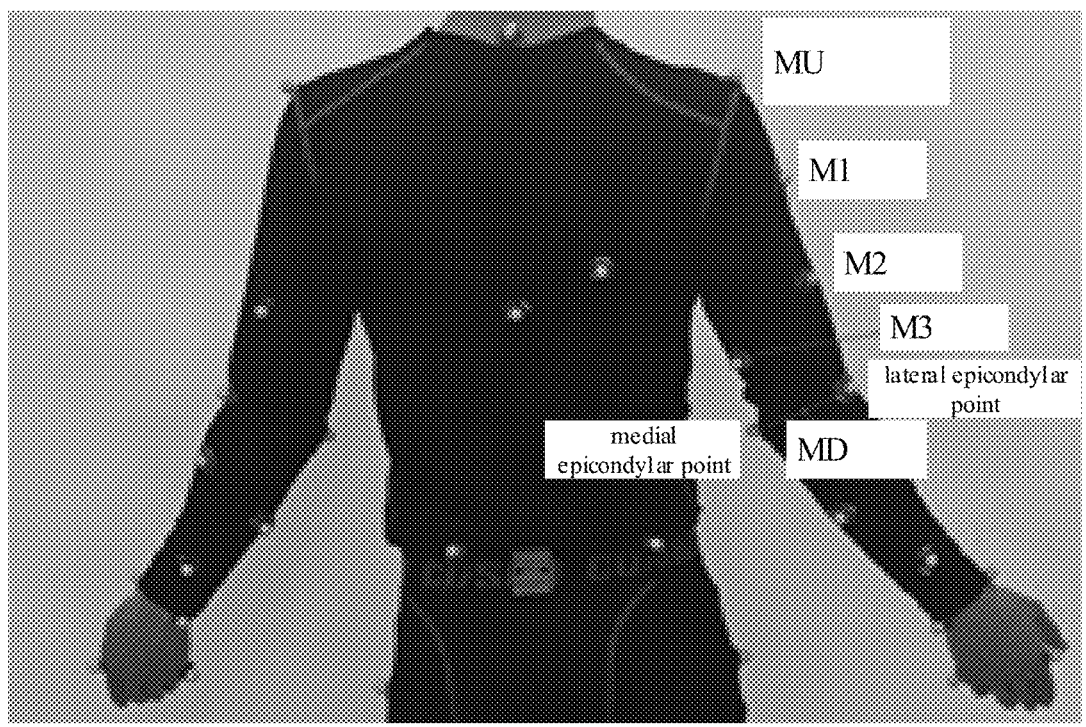
FIG. 9 is a schematic diagram of pasting positions of the marking points on the human upper arm during an experiment of the embodiment shown in FIG. 8 of the positioning method of functional rotation center of shoulder based on rigid upper arm model according to the present invention.

A measurement of upper arm angle requires an upright trunk, and in order to make scapulae participate in the upper arm movement as little as possible, gaits of the subjects were tested. 71 marking points were pasted on the subjects, FIG. 9 shows pasting positions of the marking points on the human upper arm. During the experiment, the test period was 30 s, during the test period, the subjects made actions such as standing, walking and turning, and 3000 frames of position information of each marking point were collected.

In process of positioning and analysis of FRCS, six marking points are used for each arm, namely: acromion point, medial and lateral epicondyle points of humerus and three marking points on the upper arm. The pasting positions of the three marking points M1, M2 and M3 on the upper arm meet two rules: (1) the three points can't be in a straight line; (2) the distance between the three points should be as large as possible. In this embodiment, the pasting positions of the three points not only conform to the above two rules, but also ensure that projections of the three marking points on a cross section of the upper arm divide the cross section circle into three equal parts as much as possible. In order to simplify calculation and verify results, overhead point, neck point, upper chest point, lower chest point and thoracic vertebrae points corresponding to a height of the lower chest point can be added.

Figure 10:
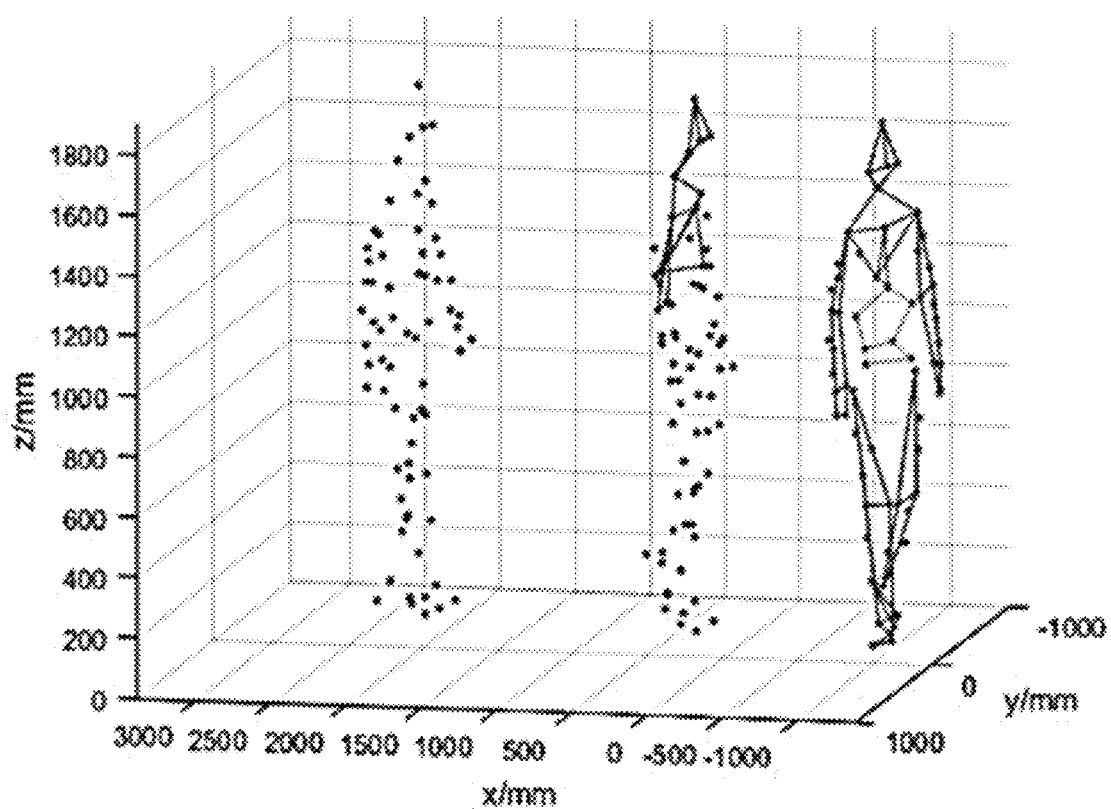
FIG. 10 is a data acquisition result of marking points of a subject in the embodiment shown in FIG. 8 of the positioning method of functional rotation center of shoulder based on rigid upper arm model according to the present invention.
Figure 11:
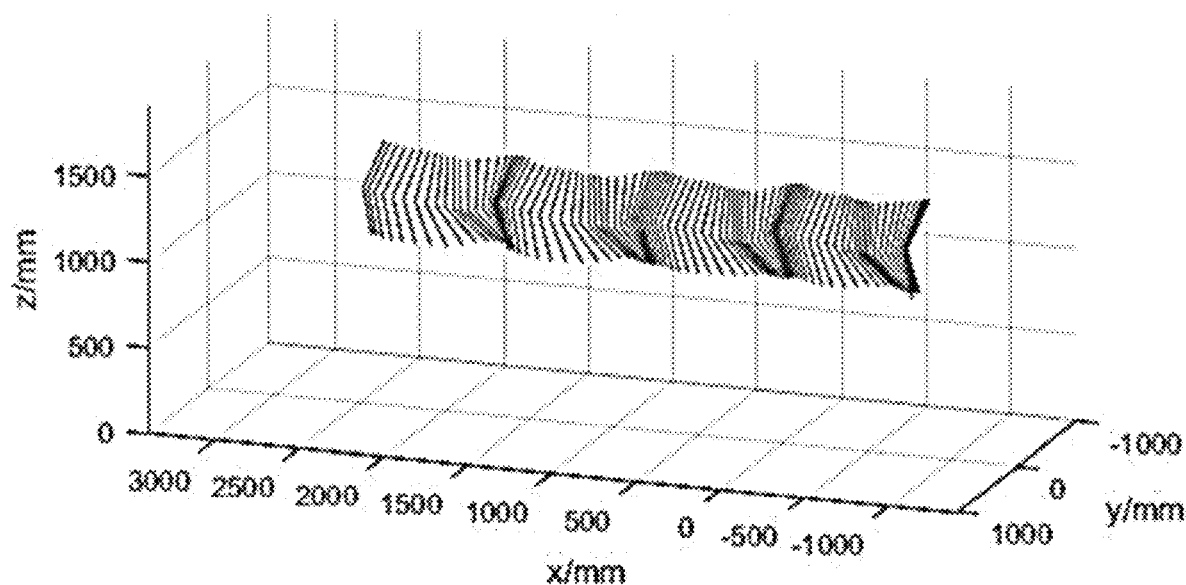
FIG. 11 is a motion trajectory of a right upper arm of a subject in the embodiment shown in FIG. 8 of the positioning method of functional rotation center of shoulder based on rigid upper arm model according to the present invention.

FIG. 10 shows a data acquisition result of the marking points of a subject, and FIG. 11 shows a motion trajectory of a right upper arm of a subject, it can be found that the upper arm of the subject performs not only rotational motion, but also translational motion.

Analysis of Experimental Results

Figure 12:
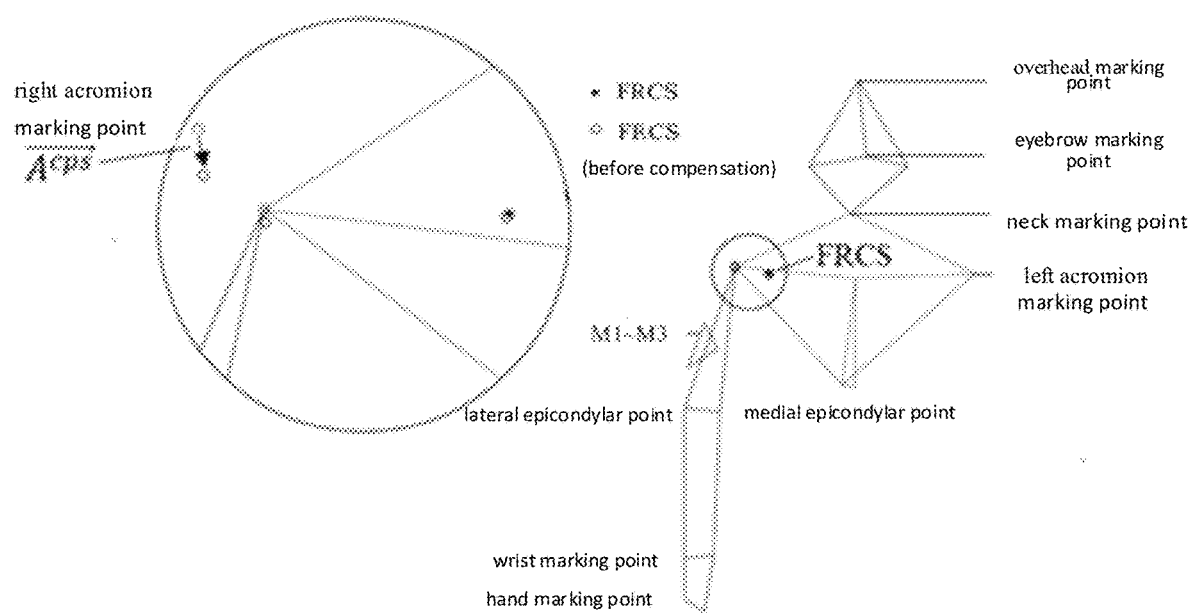
FIG. 12 is a schematic diagram of a relative position in trunk of the FRCS positioning result of subject No. 1 in the embodiment shown in FIG. 8 of the positioning method of functional rotation center of shoulder based on rigid upper arm model according to the present invention.

Taking subject No. 1 as an example, FIG. 12 shows a relative position in trunk of the FRCS positioning result, the calculation result shows that the FRCS of right shoulder is about 5 cm closer to the left acromion, about 1 cm lower than the right acromion and 0.5 cm behind the right acromion. Table 2 shows correction $\overrightarrow{A^{cps}}$ of the central axis of the cylinder of subject No. 1 at some moments.

TABLE 2 components of the correction $\overline{A^{cps}}$ of the central axis of the cylinder of subject No. 1 at some moments

| | $\overline{A^{cps}}$ ($\overline{A^{rm'}} - \overline{A^{rm}}$) | | |
|---|---|---|---|
| t/s | x/mm | y/mm | z/mm |
| 11.9900 | −2.9456 | 1.9101 | −0.8819 |
| 12.0000 | −2.7625 | 1.9091 | −0.8211 |
| 12.0100 | −2.7484 | 1.6856 | −0.8668 |
| 12.0200 | −2.7570 | 1.8888 | −0.8453 |
| 12.0300 | −2.7441 | 1.7802 | −0.8691 |
| 12.0400 | −2.6961 | 1.8211 | −0.8535 |
| 12.0500 | −2.6920 | 1.9239 | −0.8460 |
| 12.0600 | −2.6027 | 2.0851 | −0.7835 |
| . | . | . | . |
| . | . | . | . |
| 16.9500 | −1.69514 | −3.24737 | −0.93132 |
| 16.9600 | −1.47387 | −3.04155 | −0.84052 |
| 16.9700 | −1.25583 | −3.20395 | −0.83312 |
| 16.9800 | −1.23593 | −3.33113 | −0.8498 |
| Average | −1.1698 | 0.4765 | −0.5088 |
| S.D. | 1.6467 | 1.4763 | 0.5291 |

Figure 13:
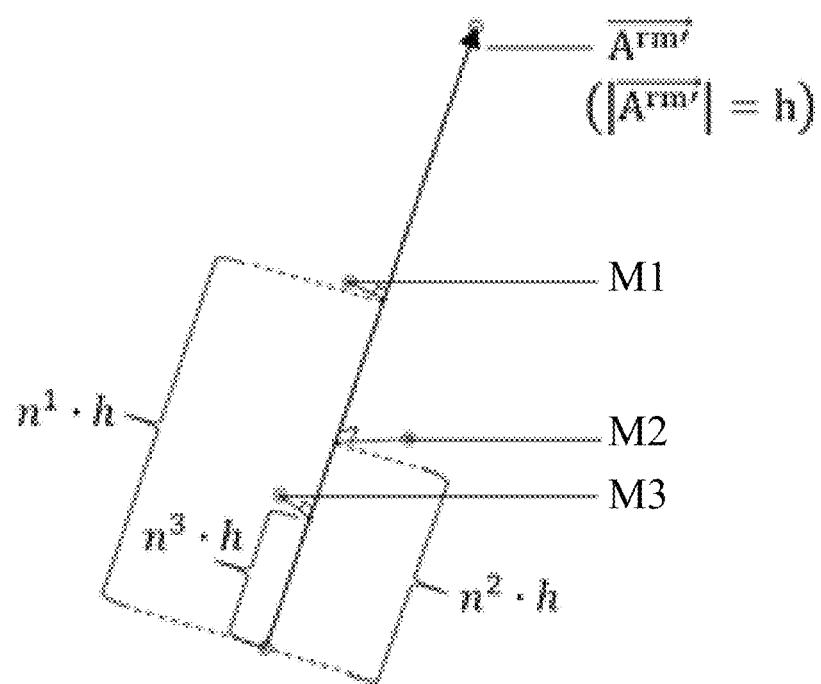
FIG. 13 shows coefficients n1, n2 and n3 of three marking points M1, M2 and M3 on the upper arm to a corrected axis vector for the subject No. 1 in the embodiment shown in FIG. 8 of the positioning method of functional rotation center of shoulder based on rigid upper arm model according to the present invention.
Figure 14:
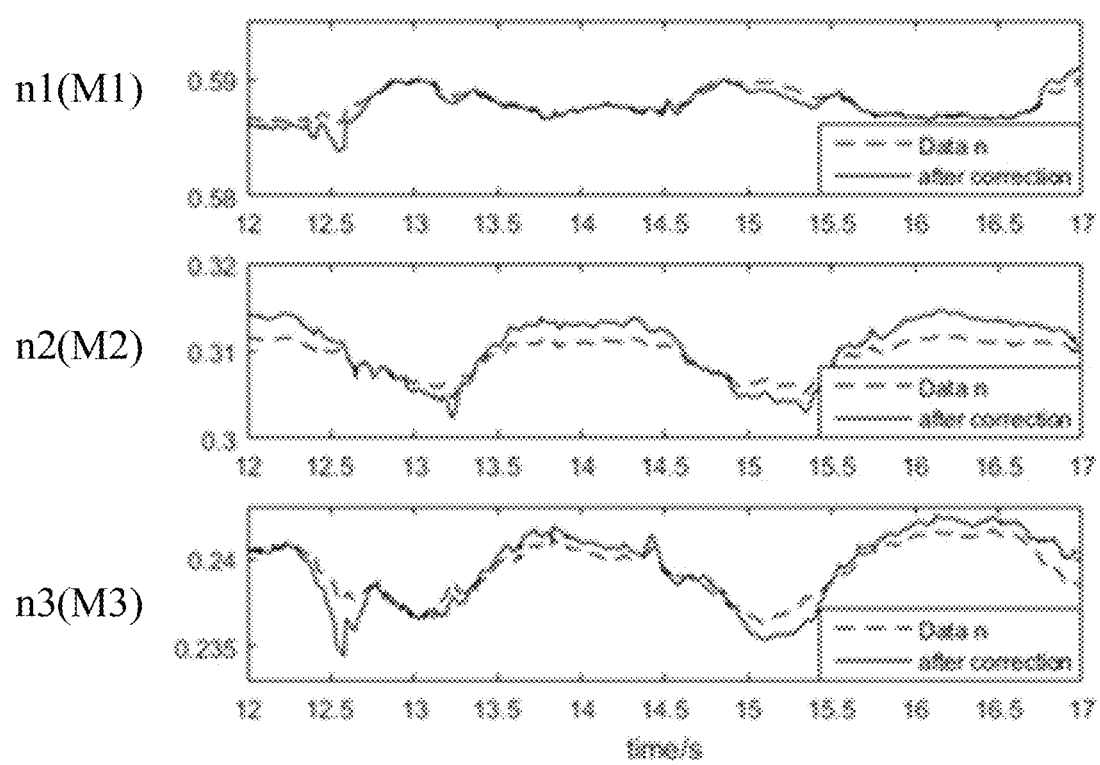
FIG. 14 shows variation trend of the coefficients n1, n2 and n3 of the three marking points M1, M2 and M3 on the upper arm to the axis vectors before and after correction during test time for the subject No. 1 in the embodiment shown in FIG. 8 of the positioning method of functional rotation center of shoulder based on rigid upper arm model according to the present invention.

For subject No. 1, FIG. 13 shows the coefficient n of the three marking points M1, M2 and M3 on the upper arm to a corrected axial vector, FIG. 14 shows variation trend of the coefficient n of the three marking points M1, M2 and M3 on the upper arm to the axis vector before and after correction during the test time, table 3 shows statistical parameters of the coefficient n of the three marking points M1, M2 and M3 on the upper arm to the axis vector before and after correction.

TABLE 3 comparison of coefficient n before and after correction of the axis vector of the upper arm

|  | (11.99 s-16.98 s) | Avg. | S.D. | Max. | Min. | Max.-Min. |
|---|---|---|---|---|---|---|
| coefficient | mark1 | 0.5878 | 0.0013 | 0.5910 | 0.5839 | 0.0071 |
| n before | mark2 | 0.3105 | 0.0034 | 0.3147 | 0.3023 | 0.0124 |
| correction | mark3 | 0.2395 | 0.0021 | 0.2425 | 0.2344 | 0.0081 |
| coefficient | mark1 | 0.5879 | 0.0011 | 0.5901 | 0.5861 | 0.0040 |
| n after | mark2 | 0.3095 | 0.0020 | 0.3119 | 0.3045 | 0.0074 |
| correction | mark3 | 0.2394 | 0.0015 | 0.2417 | 0.2363 | 0.0054 |

Figure 15:
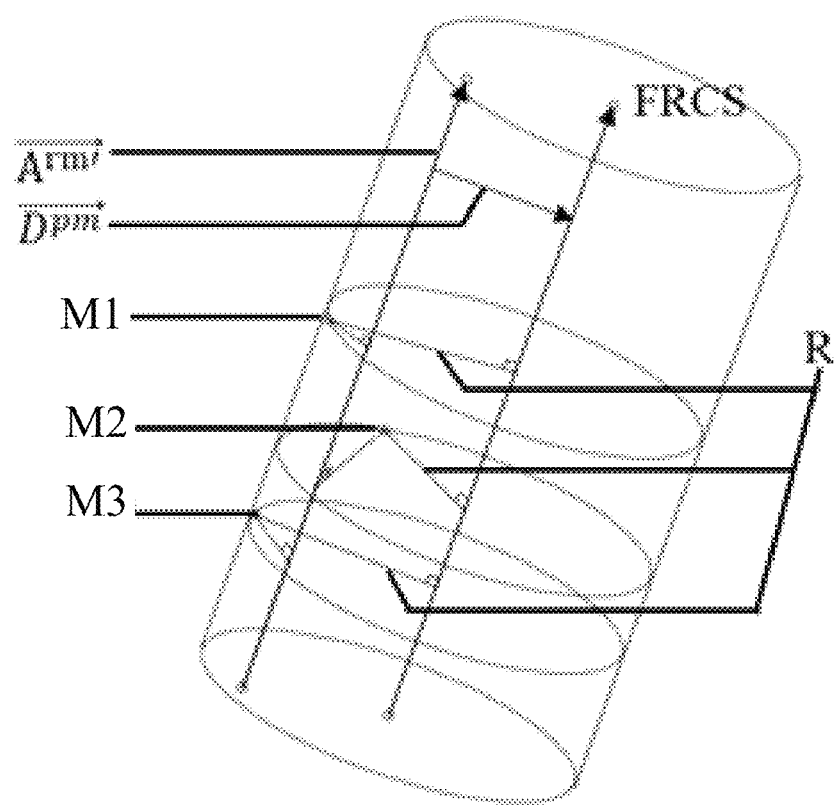
FIG. 15 is a schematic diagram of translation correction of a central axis position of the embodiment shown in FIG. 8 of the positioning method of functional rotation center of shoulder based on rigid upper arm model according to the present invention.

FIG. 15 shows a translation correction of a central axis position, wherein the translation $\vec{D}^{pm}$ is the translation correction amount of the axis vector; R is the radius of the rigid cylinder of the upper arm, and statistical parameters of R are shown in table 4.

TABLE 4 radius R of the upper arm

| R/mm | (11.99 s-16.98 s) |
|---|---|
| Average | 40.2043 |
| S.D. | 2.323 |
| Max. | 44.3065 |
| Min. | 36.4731 |

Figure 16:
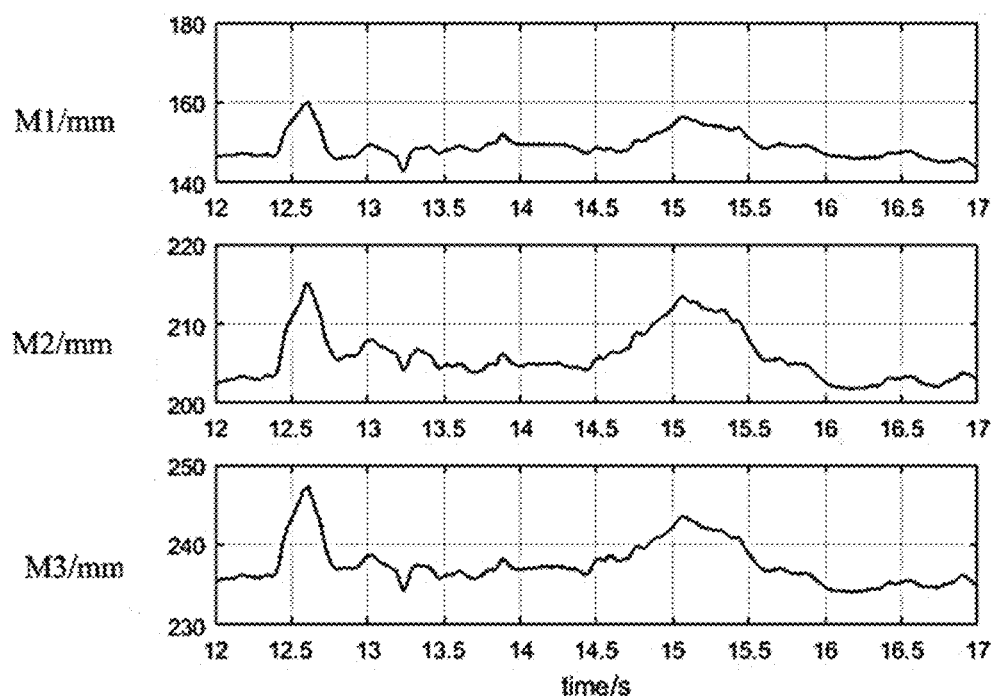
FIG. 16 shows before compensation, variations of distance from the FRCS positioning result to the three marking points M1, M2 and M3 on the upper arm for the subject No. 1 in the embodiment shown in FIG. 8 of the positioning method of functional rotation center of shoulder based on rigid upper arm model according to the present invention.
Figure 17:
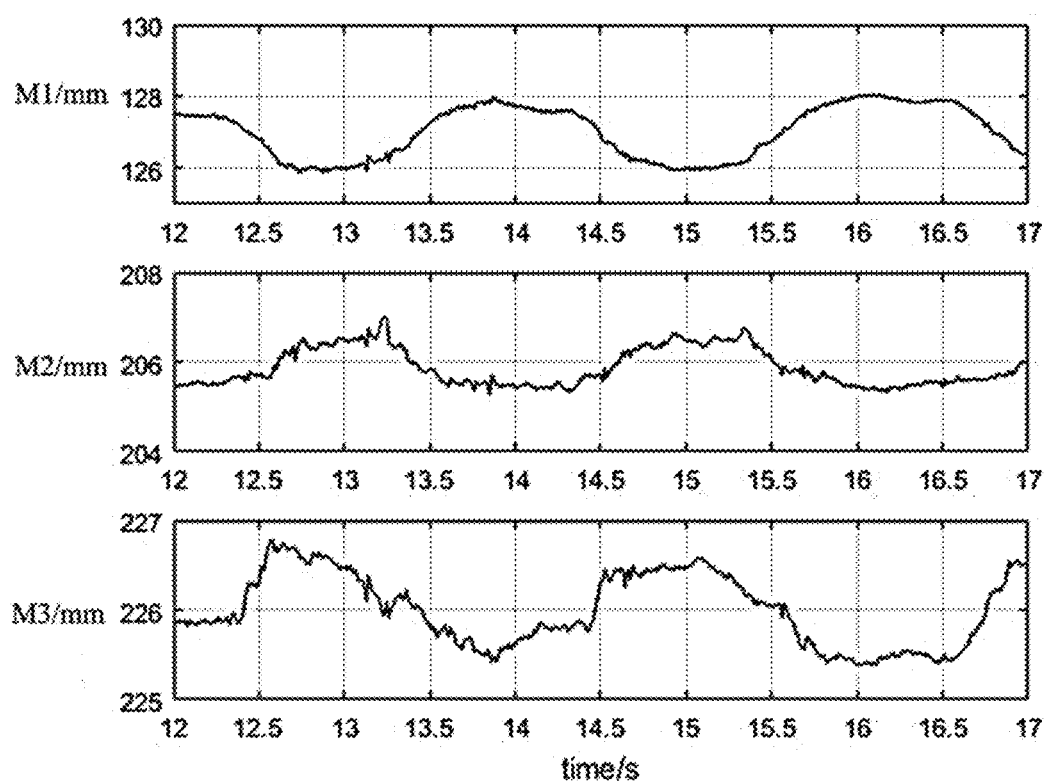
FIG. 17 shows after compensation, variations of distance from the FRCS positioning result to the three marking points M1, M2 and M3 on the upper arm for the subject No. 1 in the embodiment shown in FIG. 8 of the positioning method of functional rotation center of shoulder based on rigid upper arm model according to the present invention.

FIG. 16 shows before compensation, variations of distances from the FRCS positioning result to the three marking points M1, M2 and m3 on the upper arm, variation trends of these three distances are very similar, and standard deviations of these three distances are 3.0763 mm, 2.9816 mm and 2.5329 mm respectively; FIG. 17 shows after compensation, variations of distances from the FRCS to the three marking points M1, M2 and m3 on the upper arm, and standard deviations of these three distances are reduced to 0.7202 mm, 0.4144 mm and 0.3971 mm respectively.

Table 5 shows a scaling coefficient $l'^{rm}$ of the height of the cylinder during the compensation process.

TABLE 5 scaling coefficient $l'^{rm}$ of the height of the cylinder

| $l'^{rm}$ | (11.99 s-16.98 s) |
|---|---|
| Average | 1.0000 |
| S.D. | 0.0029 |
| Max. | 1.0047 |
| Min. | 0.9909 |

Figure 18:
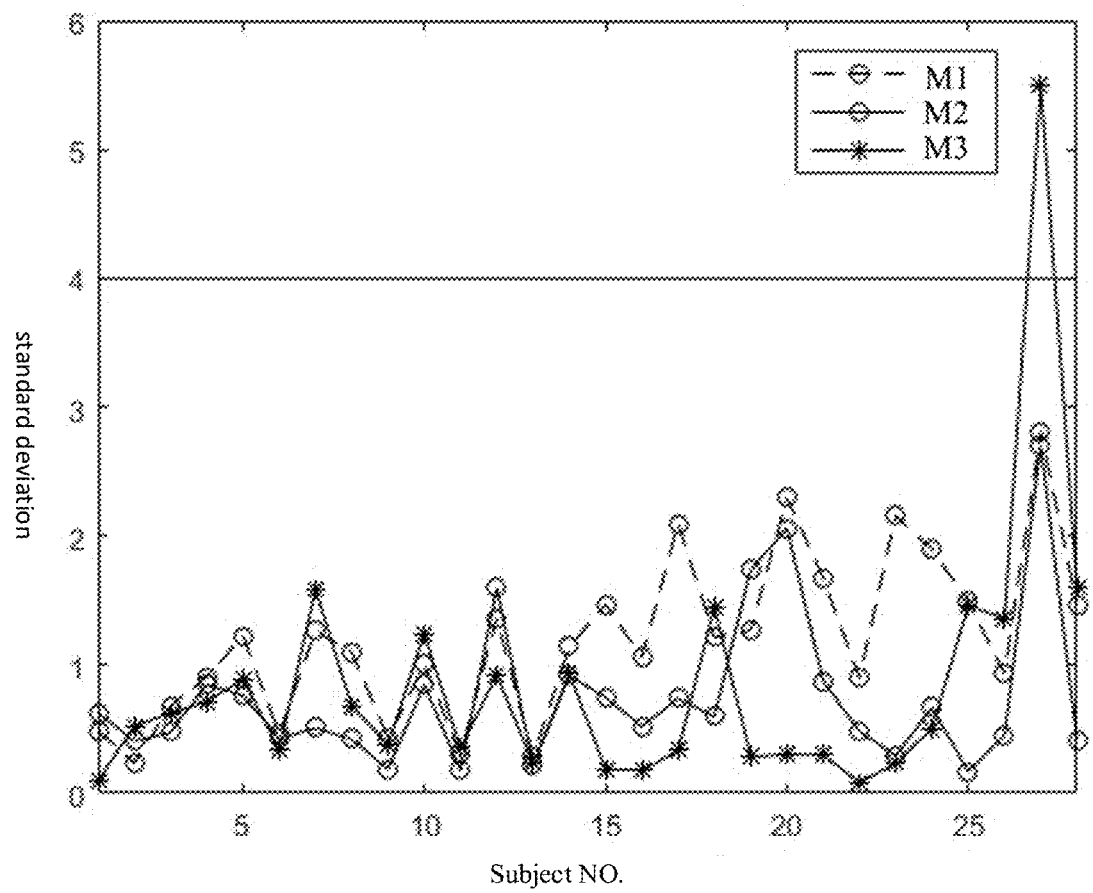
FIG. 18 shows standard deviation of variations of distance from the FRCS positioning result to the three marking points on the upper arm for right shoulders of 28 subjects in the embodiment shown in FIG. 8 of the positioning method of functional rotation center of shoulder based on rigid upper arm model according to the present invention.

FRCS is the rotation center of the upper arm in motion, ideally, the distances from FRCS to the three marking points M1, M2 and m3 in the upper arm should be consistent respectively, therefore, a standard deviation in the process of distance change is very important to describe a reliability of the method. FIG. 18 shows the standard deviations in the process of distance change from the FRCS positioning result to the three marking points on the upper arm for right shoulders of 28 subjects, wherein error of subject No. 27 is unreasonable, especially the error of the third marking point is much more than a sum of an average value and triple standard deviation, this may be caused by violent shaking caused by weak pasting of the marking point in the experiment, table 6 records relevant values of the standard deviations of changing distance from the FRCS to the marking point for the other 27 subjects during the test.

It can be seen from FIG. 16-18 and table 6 that for the positioning method of FRCS provided by the present invention, the standard deviations of the changing distance from the FRCS positioning result to the three marking points M1, M2 and M3 on the upper arm is between 0.081 and 2.2973, indicating that the positioning method of FRCS provided by the present invention has high accuracy and reliability, the positioning result of FRCS has better stability relative to the upper arm and trunk, and can be used to establish a more accurate human digital dynamic model and predict more accurate human posture.

TABLE 6 the standard deviations of changing distance from the FRCS to the three marking points for 27 subjects during the test
standard deviations of changing distance from the FRCS to the three marking points

| standard deviation/mm | average | max | min | S.D. |
|---|---|---|---|---|
| M1 | 1.1396 | 2.2973 | 0.2397 | 0.5763 |
| M2 | 0.6718 | 2.0618 | 0.1704 | 0.4651 |
| M3 | 0.6582 | 1.6031 | 0.081 | 0.4923 |

It should be noted that the above embodiments are only used to illustrate the technical solutions of the present invention, but not to limit them; although the foregoing embodiments have been described in detail, those skilled in the art should understand that they can modify recorded technical solutions in the foregoing embodiments or equivalently replaced some or all of the technical features, and these replacements do not cause the essence of the corresponding technical solutions to deviate from the scope of the technical solutions of the present invention.

What is claimed is:

1. A positioning method of a functional rotation center of a shoulder (FRCS) based on a rigid upper arm model, comprising:

step 1: abstracting a human upper arm of a particular human into a cylinder with the FRCS as a center of a top surface of the cylinder, wherein a side surface of the cylinder models a skin surface of the human upper arm;

step 2: determining a reference axis vector of the cylinder by measuring a motion of the human upper arm;

step 3: determining a central axis vector of the cylinder and, for each given moment of a plurality of moments during the measured motion, a displacement from the reference axis vector to the central axis vector, wherein, the reference axis vector is translated in a direction perpendicular to a reference direction of the cylinder, to determine the central axis vector, wherein an amount of translation is defined by a vector $\vec{D}^{pm}$ and a distance from the central axis vector to each point on the skin surface of the human upper arm is equal;

step 4: correcting the central axis vector of the cylinder;

step 5: determining a height compensation of the cylinder by stretching a height of the cylinder to account for deformation of the human upper arm resulting from the measured motion, and positioning the FRCS of the human upper arm of said particular human based on the height compensation and on the corrected central axis vector, and displaying the positioned FRCS of the human upper arm of said particular human.

2. The positioning method of the FRCS based on the rigid upper arm model according to claim 1, wherein, in step 2, the reference axis vector is a vector $\overrightarrow{A^{rm}}$ which starts from a midpoint (MD) of medial and lateral epicondylar points of a humerus on a human surface of the human upper arm to an acromion point (MU), and a direction of the vector $\overrightarrow{A^{rm}}$ is the reference direction of the cylinder; $\overrightarrow{A^{rm}}=M^U-M^D$, wherein $M^U=[X^U\ Y^U\ Z^U]^T$ represents position information of the acromion point MU, $M^D=[X^D\ Y^U\ Z^U]^T$ represents position information of the midpoint MD of the medial and lateral epicondylar points of the humerus; for any point A on the skin surface of the human upper arm, position information of the point A from starting time $t_0$ to ending time $t_s$ expressed as $M^A$, $$M^A = \begin{bmatrix} X^A & Y^A & Z^A \end{bmatrix}^T = \begin{bmatrix} X^A_{t_0} & X^A_{t_0+\Delta t} & X^A_{t_0+2\Delta t} & \cdots & X^A_{t_s} \\ Y^A_{t_0} & Y^A_{t_0+\Delta t} & Y^A_{t_0+2\Delta t} & \cdots & Y^A_{t_s} \\ Z^A_{t_0} & Z^A_{t_0+\Delta t} & Z^A_{t_0+2\Delta t} & \cdots & Z^A_{t_s} \end{bmatrix},$$

wherein $t_s=t_0+k\Delta t$, $k \geq 3$, $\Delta t$ is a sampling interval.

3. The positioning method of the FRCS based on the rigid upper arm model according to claim 1, wherein, in step 3, an end point of the central axis vector is the FRCS, and position information of the FRCS is expressed as:

$$RCS^F = M^U + \overrightarrow{D^{pm}} \qquad (1)$$

wherein $M^U$ represents position information of an acromion point.

4. The positioning method of the FRCS based on the rigid upper arm model according to claim 3, wherein, step 3 comprises:
step 31: determining three marking points M1, M2 and M3 on the skin surface of the human upper arm, and vertical vectors $\overrightarrow{R^1}$, $\overrightarrow{R^2}$, and $\overrightarrow{R^3}$ respectively from the marking points M1, M2 and M3 to the reference axis vector being translated to make a start point of each of the vertical vectors be located at a midpoint MD of the medial and lateral epicondylar points of the humerus;
step 32: determining a center of a circle where an end point of each of the vertical vectors is located after a translation (represented by mark O), a displacement from the midpoint MD of the medial and lateral epicondyle points of the humerus to the center O being $\overrightarrow{D^{pm}}$ denoting a displacement from the reference axis vector to the central axis vector.

5. The positioning method of the FRCS based on the rigid upper arm model according to claim 3, wherein, in step 3, for a time $t_a$ in a process, a coordinate system is translated to establish a local coordinate system, wherein the local coordinate takes $M_{t_a}^D = [X_{t_a}^D\ Y_{t_a}^D\ Z_{t_a}^D]^T$ a coordinate origin, then, at the time $t_a$, reverse vectors $\overrightarrow{R_{t_a}^n}$ of vertical vectors respectively from marking points M1, M2 and M3 to the reference axis vector satisfy a relational formula $\overrightarrow{R_{t_a}^n} = R_{t_a}^n - 0$, wherein, $R_{t_a}^n$ represent end coordinates of the vectors $\overrightarrow{R_{t_a}^n}$, n=1, 2, 3.

6. The positioning method of the FRCS based on the rigid upper arm model according to claim 5, wherein, according to formula $$\begin{vmatrix} O_{xt_a} & O_{yt_a} & O_{zt_a} & 1 \\ R_{xt_a}^1 & R_{yt_a}^1 & R_{zt_a}^1 & 1 \\ R_{xt_a}^2 & R_{yt_a}^2 & R_{zt_a}^2 & 1 \\ R_{xt_a}^3 & R_{yt_a}^3 & R_{zt_a}^3 & 1 \end{vmatrix} = 0 \qquad (4)$$

and formula $$(R_{xt_a}^1 - O_{xt_a})^2 + (R_{yt_a}^1 - O_{yt_a})^2 + (R_{zt_a}^1 - O_{zt_a})^2 = \qquad (5)$$
$$(R_{xt_a}^2 - O_{xt_a})^2 + (R_{yt_a}^2 - O_{yt_a})^2 + (R_{zt_a}^2 - O_{zt_a})^2 =$$
$$(R_{xt_a}^3 - O_{xt_a})^2 + (R_{yt_a}^3 - O_{yt_a})^2 + (R_{zt_a}^3 - O_{zt_a})^2,$$

determining coordinates $O_{t_a} = [O_{xt_a}\ O_{yt_a}\ O_{zt_a}]^T$ of the center O at the time $t_a$, restoring the coordinates $O_{t_a} = [O_{xt_a}\ O_{yt_a}\ O_{zt_a}]^T$ to a global coordinate system, wherein the vector $\overrightarrow{A_{t_a}^{rm}}$ is translated to make a starting point of the vector $A^{rm}$ coincide with the $O_{t_a}$ to obtain a translation $\overrightarrow{D^{pm}}$, at this time, an end point of the vector $\overrightarrow{A_{t_a}^{rm}}$ after the translation is a position of the FRCS.

7. The positioning method of the FRCS based on the rigid upper arm model according to claim 6, wherein, in step 4, the central axis vector of the cylinder is corrected by introducing a proportion coefficient n of a height of the marking points on the skin surface of the human upper arm in the cylinder to a total height of the cylinder.

8. The positioning method of the FRCS based on the rigid upper arm model according to claim 7, wherein, step 4 comprises:
step 41: projecting the three marking points M1, M2 and M3 on the skin surface of the human upper arm to the reference axis vector, for a time $t_a$ in the process, there being relational formulas $$\begin{cases} n_{t_a}^{fir} \overrightarrow{A_{t_a}^{rm}} + \overrightarrow{R_{t_a}^1} = M_{t_a}^1 - M_{t_a}^D \\ n_{t_a}^{sec} \overrightarrow{A_{t_a}^{rm}} + \overrightarrow{R_{t_a}^2} = M_{t_a}^2 - M_{t_a}^D \\ n_{t_a}^{thd} \overrightarrow{A_{t_a}^{rm}} + \overrightarrow{R_{t_a}^1} = M_{t_a}^3 - M_{t_a}^D \end{cases} \qquad (6)$$

and $$\begin{cases} \overrightarrow{A_{t_a}^{rm}} \cdot \overrightarrow{R_{t_a}^1} = 0 \\ \overrightarrow{A_{t_a}^{rm}} \cdot \overrightarrow{R_{t_a}^2} = 0 \\ \overrightarrow{A_{t_a}^{rm}} \cdot \overrightarrow{R_{t_a}^3} = 0 \end{cases} \qquad (7)$$

wherein $\overrightarrow{R_{t_a}^1}$ represents a vector starting from a perpendicular foot from the marking point M1 to a vector $\overrightarrow{A_{t_a}^{rm}}$ and pointing to the marking point M1 at the time $t_a$, $\overrightarrow{R_{t_a}^2}$ presents a vector starting from a perpendicular foot from the marking point M2 to the vector $\overrightarrow{A_{t_a}^{rm}}$ and pointing to the marking point M2 at the time $t_a$, $\overrightarrow{R_{t_a}^3}$ presents a vector starting from a perpendicular foot from the marking point M3 to the vector $\overrightarrow{A_{t_a}^{rm}}$ and pointing to the marking point M3 at the time $t_a$; $n_{t_a}^{fir}$, $n_{t_a}^{sec}$ and $n_{t_a}^{thd}$ respectively represent ratios of vectors starting from MD and pointing to perpendicular feet from the marking points M1, M2 and M3 to the vector $\overrightarrow{A_{t_a}^{rm}}$ at the time $t_a$; $M_{t_a}^1$ represents position coordinates of the marking point M1 at the time $t_a$, $M_{t_a}^2$ represents position coordinates of the marking point M2 at the time $t_a$, $M_{t_a}^3$ represents position coordinates of the marking point M3 at the time $t_a$, $M_{t_a}^D$ represents position coordinates of the midpoint MD at the time $t_a$, and $M_{t_a}^U$ represents position coordinates of the acromion point at the time $t_a$;

step 42: marking $n^{fir}=[n_{t_0}^{fir}\ n_{t_0+\Delta t}^{fir}\ n_{t_0+2\Delta t}^{fir}\ \ldots\ n_{t_S}^{fir}]$, $$n^{al} = \begin{bmatrix} n^{fir} \\ n^{sec} \\ n^{thd} \end{bmatrix},$$

in combining formulas ⑥ with formula ⑦, and obtaining that at the time $t_a$:

$$n_{t_a}^{al} = \begin{bmatrix} (M_{t_a}^1 - M_{t_a}^D)^T \\ (M_{t_a}^2 - M_{t_a}^D)^T \\ (M_{t_a}^3 - M_{t_a}^D)^T \end{bmatrix} \cdot (M_{t_a}^U - M_{t_a}^D) \cdot ((M_{t_a}^U - M_{t_a}^D)^T \cdot (M_{t_a}^U - M_{t_a}^D))^{-1};$$

step 43: selecting a proportion coefficient $n_{t_j}^{al}$ at time $t_j$ when arms are vertically downward in a human standing posture as a standard coefficient, adding a correction amount $\overrightarrow{A_{ta}^{cps}}$ to the $\overrightarrow{A_{t_a}^{rm}}$ at the a time $t_a$ to make:

$$n^{al'} = \begin{bmatrix} n_{t_j}^{fir} \cdot [1\ 1\ \ldots\ 1] \\ n_{t_j}^{sec} \cdot [1\ 1\ \ldots\ 1] \\ n_{t_j}^{thd} \cdot [1\ 1\ \ldots\ 1] \end{bmatrix}$$

wherein $n^{al'}$ and $\overrightarrow{A_{t_a}^{rm'}}$ after corrected meet requirements of formulas ④ and ⑤;

step 44: according to the correction amount $\overrightarrow{A_{ta}^{cps}}$ without changing modulus $|\overrightarrow{A_{t_a}^{rm}}|$ of the central axis vector, obtaining $|\overrightarrow{A_{t_a}^{rm'}}|$ as follows:

$$|\overrightarrow{A_{t_a}^{rm'}}| = |\overrightarrow{A_{t_a}^{rm}} + \overrightarrow{A_{t_a}^{cps}}| = |\overrightarrow{A_{t_a}^{rm}}| \quad (⑧);$$

step 45: in a conical generatrix set satisfying a first column of formula ⑥, a first column of formula ⑦, and formula ⑧, a conical generatrix set satisfying a second column of formula ⑥, a second column of formula ⑦, and formula ⑧, and a conical generatrix set satisfying a third column of formula ⑥, a third column of formula ⑦, and formula ⑧, respectively selecting solutions and combining the solutions to obtain $\overrightarrow{A_{t_a}^{rm'}}$, and then obtaining a final correction $\overrightarrow{A_{ta}^{cps}}$, according to the final correction $\overrightarrow{A_{ta}^{cps}}$, rewriting formula ① as:

$$RCS^F = M^U + \overrightarrow{A^{cps}} + \overrightarrow{D^{pm}} \quad ⑬$$

wherein $\overrightarrow{D^{pm}}$ is resolved according to an axis vector $\overrightarrow{A^{rm'}}$ in a correction direction.

9. The positioning method of the FRCS based on the rigid upper arm model according to claim 8, wherein, in step 5, after determining the height compensation of the cylinder, a final calculation formula of the FRCS is:

$$RCS^F = M^U + \overrightarrow{A^{cps}} + \overrightarrow{D^{pm}} - (1 - \overrightarrow{l^{rm}})(\overrightarrow{A^{rm}} + \overrightarrow{A^{cps}}) \quad ⑰$$

wherein, the $l^{rm}$ is a height compensation coefficient of the cylinder.

\* \* \* \* \*